(12) United States Patent
Stigall et al.

(10) Patent No.: US 11,471,215 B2
(45) Date of Patent: Oct. 18, 2022

(54) DEVICE AND METHODS FOR CROSSING OCCLUSIONS

(71) Applicant: VOLCANO CORPORATION, San Diego, CA (US)

(72) Inventors: Jeremy Stigall, San Diego, CA (US); John Unser, Temecula, CA (US); Dino De Cicco, San Diego, CA (US); Maritess Minas, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 678 days.

(21) Appl. No.: 14/832,073

(22) Filed: Aug. 21, 2015

(65) Prior Publication Data
US 2016/0051323 A1     Feb. 25, 2016

Related U.S. Application Data

(60) Provisional application No. 62/040,158, filed on Aug. 21, 2014.

(51) Int. Cl.
*A61B 8/08*     (2006.01)
*A61B 8/12*     (2006.01)
(Continued)

(52) U.S. Cl.
CPC .......... *A61B 18/1492* (2013.01); *A61B 8/085* (2013.01); *A61B 8/0891* (2013.01); *A61B 8/12* (2013.01); *A61B 17/22* (2013.01); *A61B 17/32037* (2013.01); *A61B 17/320725* (2013.01); *A61B 17/320758* (2013.01); *A61B 17/3478* (2013.01); *A61B 2017/003* (2013.01); *A61B 2017/00867* (2013.01); *A61B 2017/22038* (2013.01); *A61B 2017/22041* (2013.01); *A61B 2017/22061* (2013.01); *A61B 2017/22068* (2013.01); *A61B 2017/22084* (2013.01); *A61B 2017/22094* (2013.01); *A61B 2017/22095* (2013.01); *A61B 2017/320004* (2013.01); *A61B 2018/0041* (2013.01);
(Continued)

(58) Field of Classification Search
CPC ................................ A61B 2017/22094–22095
See application file for complete search history.

(56) References Cited

U.S. PATENT DOCUMENTS

| 6,010,449 A | 1/2000 | Selmon |
| 6,911,026 B1 | 6/2005 | Hall |

(Continued)

FOREIGN PATENT DOCUMENTS

| JP | 2008508059 A | 3/2008 |
| JP | 03191543 U | 6/2014 |

(Continued)

*Primary Examiner* — Angela M Hoffa

(57) ABSTRACT

The invention provides devices with integrated intravascular imaging and methods for crossing a CTO within the true lumen of a vessel. An interventional catheter with intravascular imaging capabilities can be guided into an affected vessel and to a CTO. An included intravascular imaging device captures a 3D image of the environment. The catheter includes a crossing member that can be extended out from a distal tip of the catheter, causing the crossing member to directly cross through the CTO creating a new channel through the CTO.

24 Claims, 22 Drawing Sheets

(51) Int. Cl.
*A61B 17/22* (2006.01)
*A61B 18/14* (2006.01)
*A61B 17/3207* (2006.01)
*A61B 17/3203* (2006.01)
*A61B 90/00* (2016.01)
*A61B 17/34* (2006.01)
*A61B 17/32* (2006.01)
*A61B 17/00* (2006.01)
*A61B 18/00* (2006.01)
*A61B 18/12* (2006.01)

(52) U.S. Cl.
CPC ............ *A61B 2018/00982* (2013.01); *A61B 2018/1253* (2013.01); *A61B 2090/3735* (2016.02)

(56) References Cited

U.S. PATENT DOCUMENTS

| | | | |
|---|---|---|---|
| 7,988,646 B2* | 8/2011 | Taber | A61M 25/0082 600/585 |
| 7,993,358 B2 | 8/2011 | O'Brien | |
| 8,172,863 B2* | 5/2012 | Robinson | A61B 17/32002 606/159 |
| 8,496,679 B2* | 7/2013 | Robinson | A61B 17/32002 606/159 |
| 8,709,028 B2* | 4/2014 | Robinson | A61B 17/32002 606/159 |
| 8,764,730 B2* | 7/2014 | Taber | A61M 25/0082 600/585 |
| 8,932,315 B2* | 1/2015 | Boland, II | A61B 17/22 606/185 |
| 8,936,553 B2* | 1/2015 | Stigall | A61B 6/504 600/407 |
| 9,005,225 B2* | 4/2015 | Robinson | A61B 17/32002 606/159 |
| 9,034,004 B2* | 5/2015 | Pansky | A61B 17/22012 606/159 |
| 9,095,370 B2* | 8/2015 | Wilkinson | A61B 17/320725 |
| 9,125,683 B2* | 9/2015 | Farhangnia | A61B 17/3207 |
| 9,204,893 B2 | 12/2015 | Rizk | |
| 9,259,340 B2* | 2/2016 | Heuser | A61F 2/95 |
| 9,402,649 B2* | 8/2016 | Boland, II | A61B 17/22 |
| 10,136,914 B2 | 11/2018 | Lupton | |
| 10,166,084 B2* | 1/2019 | Ahari | A61B 90/39 |
| 10,265,206 B2* | 4/2019 | Heuser | A61M 25/0194 |
| 10,335,173 B2* | 7/2019 | Simpson | A61M 25/0194 |
| 2006/0276749 A1* | 12/2006 | Selmon | A61B 6/12 604/164.01 |
| 2006/0293612 A1 | 12/2006 | Jenson | |
| 2007/0293846 A1 | 12/2007 | Von Oepen | |
| 2008/0077165 A1* | 3/2008 | Murphy | A61B 17/320725 606/159 |
| 2008/0319386 A1* | 12/2008 | Bonnette | A61B 17/32037 604/95.02 |
| 2009/0005757 A1* | 1/2009 | Taber | A61M 25/0071 604/523 |
| 2009/0093791 A1* | 4/2009 | Heuser | A61B 17/12136 604/509 |
| 2009/0156983 A1 | 6/2009 | Bonnette | |
| 2009/0198153 A1 | 8/2009 | Shriver | |
| 2009/0264826 A1 | 10/2009 | Thompson | |
| 2011/0208222 A1* | 8/2011 | Ljahnicky | A61B 17/320758 606/159 |
| 2011/0218528 A1* | 9/2011 | Ogata | A61B 18/1492 606/33 |
| 2011/0264125 A1* | 10/2011 | Wilson | A61B 17/320016 606/159 |
| 2012/0165789 A1 | 6/2012 | Deckard | |
| 2012/0265229 A1* | 10/2012 | Rottenberg | A61B 17/3207 606/170 |
| 2012/0283565 A1 | 11/2012 | Richter | |
| 2013/0066345 A1* | 3/2013 | Wilkinson | A61B 17/320725 606/159 |
| 2013/0150716 A1* | 6/2013 | Stigall | A61B 6/504 600/439 |
| 2013/0296704 A1 | 11/2013 | Magnin | |
| 2013/0324967 A1* | 12/2013 | Pillai | A61M 25/0082 604/506 |
| 2014/0180118 A1* | 6/2014 | Stigall | A61B 8/12 600/463 |
| 2014/0276015 A1 | 9/2014 | Whiseant | |
| 2014/0350568 A1* | 11/2014 | Shekalim | A61M 25/09 606/127 |
| 2015/0141812 A1* | 5/2015 | Stigall | A61B 6/504 600/424 |
| 2015/0320975 A1* | 11/2015 | Simpson | A61B 17/22 604/510 |
| 2016/0038031 A1* | 2/2016 | Margallo | A61B 18/18 600/478 |
| 2016/0183963 A1* | 6/2016 | Richter | A61M 25/0068 606/159 |
| 2016/0235429 A1* | 8/2016 | Farhangnia | A61B 17/3207 |
| 2016/0302762 A1* | 10/2016 | Stigall | A61B 8/12 |
| 2018/0161550 A1* | 6/2018 | Pillai | A61M 25/0082 |
| 2020/0060718 A1* | 2/2020 | Patel | A61B 17/320783 |

FOREIGN PATENT DOCUMENTS

| | | |
|---|---|---|
| WO | 0245598 | 6/2002 |
| WO | 2007025230 | 3/2007 |
| WO | 2009144561 | 12/2009 |

* cited by examiner

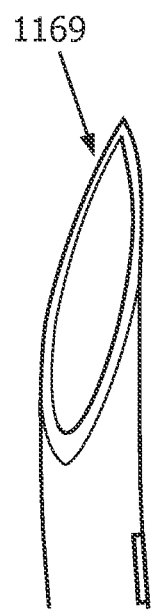
FIG. 11   FIG. 12
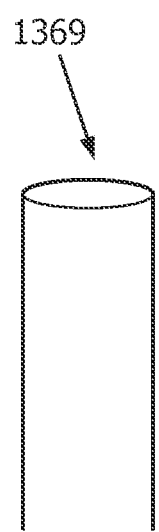
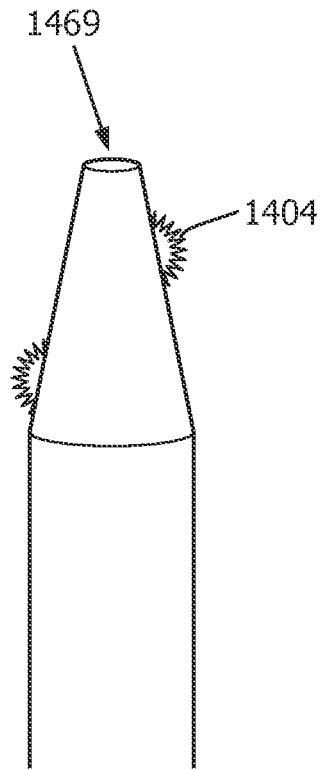
FIG. 13   FIG. 14

DEVICE AND METHODS FOR CROSSING OCCLUSIONS

RELATED APPLICATIONS

This application claims priority to and the benefit of U.S. Provisional Patent Application Ser. No. 62/040,158, filed Aug. 21, 2014, the contents of which are incorporated by reference herein in their entirety.

FIELD OF THE INVENTION

The invention relates to methods and devices for the treatment of vascular occlusions.

BACKGROUND

Sometimes a person will experience severe pain in the chest. The pain may also be felt in the neck, shoulders, or jaw. This pain may be accompanied by symptoms such as feelings of nausea or indigestion, shortness of breath, fatigue, cold-sweat, irregular heartbeat, dizziness, and an inability to be physically active. This chest pain, known as angina, is a symptom of heart disease in which a waxy plaque builds up on the walls of the arteries that need to carry oxygen-rich blood to the heart. The buildup of plaque occludes the vessels, restricting blood flow. If the plaque completely occludes a vessel, no blood can flow through that vessel.

A total occlusion that lasts for three months is defined as a chronic total occlusion (CTO). See Aziz, 2005, Chronic total occlusions, Heart 91:iii42-iii48. Typically, a CTO will have a tough fibrous cap at either end, with softer material in between. If a CTO goes untreated, the person may experience ongoing and worsening angina pain and may even die. See Shah, 2011, Management of coronary chronic total occlusion, Circulation 123:1780-1784.

On approach to treating a CTO involves inserting a wire into the lumen of the affected vessel and advancing the wire to the CTO. The wire is then used to cross through the CTO, effectively puncturing a hole through it. Rathore et al., 2009, Retrograde percutaneous recanalization of chronic total occlusion of the coronary arteries: Procedural outcomes and predictors of success in contemporary practice. Circ Cardiovascular Interv, 2:124-132. In contrast to collateral and subintimal strategies, this approach is sometimes described as "true lumen" CTO crossing. Unfortunately, a true lumen crossing procedure carries serious risks of complications such as thrombosis, dissection of the arteries, collateral perforation, and even equipment entrapment, any of which can be life-threatening. Further complications include injury to the arteries, global ischemia, and hemodynamic deterioration.

SUMMARY

The invention provides methods for crossing a CTO within the true lumen of a vessel using an interventional catheter apparatus that has integrated intravascular imaging to aid in avoiding complications associated with true lumen CTO crossing. The interventional catheter apparatus with intravascular imaging capabilities can be guided through a patient's vasculature, into an affected vessel, and brought to a CTO. An included intravascular imaging device can capture a 3D image of the environment, aiding a practitioner in seeing the position of the catheter for CTO crossing. The interventional imaging catheter can also include a centering device, giving the practitioner a tool for biasing the catheter away from a vessel wall. The catheter includes a crossing member such as a needle or needle-tipped crossing wire and the practitioner can extend the crossing member out from a distal tip of the catheter, causing the tip to directly cross through the CTO creating a new channel through the CTO. This can be followed by using ablation devices, balloons, or other tools to re-open the true lumen through the affected vessel. Since the catheter provides a tool for successfully crossing a CTO, a patient will not experience chronic angina pain and symptoms and even death can be avoided. Since the catheter includes tools for imaging and centering the apparatus prior to and during CTO crossing, adverse complications such as collateral perforation and artery dissection are avoided. Undesirable thrombosis, global ischemia, and hemodynamic deterioration are minimized and true lumen CTO crossing is made safer and more effective. Thus with devices of the invention, patient's lives are improved and even saved with relief from angina and its symptoms being provided.

In certain aspects, the invention provides an apparatus for crossing a chronic total occlusion (CTO). The apparatus includes a catheter with an extended body configured for insertion into a vessel of a patient, an intravascular imaging device on a distal portion of the extended body, and an exit port on a distal end of the extended body. The exit location is preferably close to the imaging apparatus and may be just proximal to the imaging apparatus. In some embodiments, the exit location is distal to the imaging apparatus. A crossing member is disposed within a lumen in the catheter and configured to be pushed out of the exit port and extend away from the distal end of the extended body. The crossing member may define a stiff CTO wire or may define an extended needle or needle-tipped wire. Preferably, the lumen extends throughout a length of the catheter in an over-the-wire configuration. The apparatus may also include a guidewire lumen, e.g., extending along a portion of the length of the catheter in a rapid exchange configuration. The crossing member is stiff for crossing the CTO and using flexural modulus as a measure of stiffness, the crossing member may have a flexural modulus of at least 20 GPa. A tip of the crossing member is configured to cross through the CTO within a true lumen of the vessel. The tip may be sharpened, a needle, multi-pronged, or blunt and may include one or more burrs to grip and disrupt the fibrous CTO cap. In some embodiments, the tip defines at least two prongs to better break through the fibrous cap. Additionally or alternatively, the apparatus may include a steerable or deflectable tip. A deflectable tip mechanism may be included to steer the tip towards an area of interest. A shape set material such as shape set nitinol, e.g., with a telescoping feature, can encourage the deflection. The tip may be influenced by the shape setting of the material to effectively steer in the intended direction.

In certain alternative embodiments, the apparatus has inherent rigidity to cross a CTO and need not include a lumen. For example, the device may have a high flexural modulus as described herein and the apparatus need not include a wire or crossing member.

The apparatus may further include features to aid in crossing the CTO or avoiding damage. For example, the apparatus may include a spring mechanism that exerts force on the crossing member to push the tip through the CTO. The apparatus may include a balloon for treatment, like a non-compliant balloon or a drug-eluting balloon for treatment of the site.

In certain embodiments, the apparatus includes a mechanism to bias the body of the apparatus away from a vessel wall (e.g., towards a center of the vessel). The mechanism may define a self-centering feature such as a balloon or an expandable funnel braid. The mechanism may define a helical cage apparatus.

The apparatus can include an RF energy delivery system. The tip may be configured to deliver RF energy to disrupt the CTO. In certain embodiments, the tip delivers the RF energy via a monopolar mechanism using at least one electrode placed outside of a body of the patient. An electrode may be located within the device for RF energy.

In some embodiments, the apparatus cuts through the CTO with the aid of a fluid jet. The inclusion of one or more fluid jet can support hydro-dissection, lytic disbursement, or both. The apparatus includes a jet to deliver fluid to cut through the CTO using, for example, a jet lumen extending through, around, or adjacent the crossing member. Other features that may be provided with the apparatus include a cutting balloon, deflectable tip, or drug delivery. A cutting balloon includes sharp edges on a surface of the balloon. When the balloon is inserted into the CTO and inflated the edges aid in breaking up the CTO. The apparatus may include a deflectable tip mechanism to steer the tip towards an area of interest. In some embodiments, the apparatus uses a lumen (e.g., through the crossing member or through the catheter) as a mechanism for injecting agent through the tip of the crossing member into a cap of the CTO. Suitable agents include thrombolytic drugs or an agent to dissolve the CTO such as ethanol.

In related aspects, the invention provides a method for crossing a CTO. An intravascular imaging apparatus is inserted into an occluded vessel of a patient. The apparatus includes a catheter with an extended body and an intravascular imaging device disposed on a distal portion thereof. At a distal end of extended body is an exit port. The imaging device is used for imaging the vessel to obtain a 3D image. A crossing member disposed within a lumen in the catheter is extended from the catheter, away from the distal end of the extended body, and used to cross through the CTO.

BRIEF DESCRIPTION OF THE DRAWINGS

FIG. 11 illustrates a tip that defines a sharpened point.
FIG. 12 illustrates a tip that is intermediate between pointed and blunt.
FIG. 13 illustrates a blunt tip.
FIG. 14 describes a tip with one or more burs.

DETAILED DESCRIPTION

The invention provides an intravascular imaging catheter apparatus for direct crossing of a CTO. An apparatus of the invention can pierce through the CTO directly (true lumen crossing) and also provide an intravascular image of the affected vessel.

Figure 1:
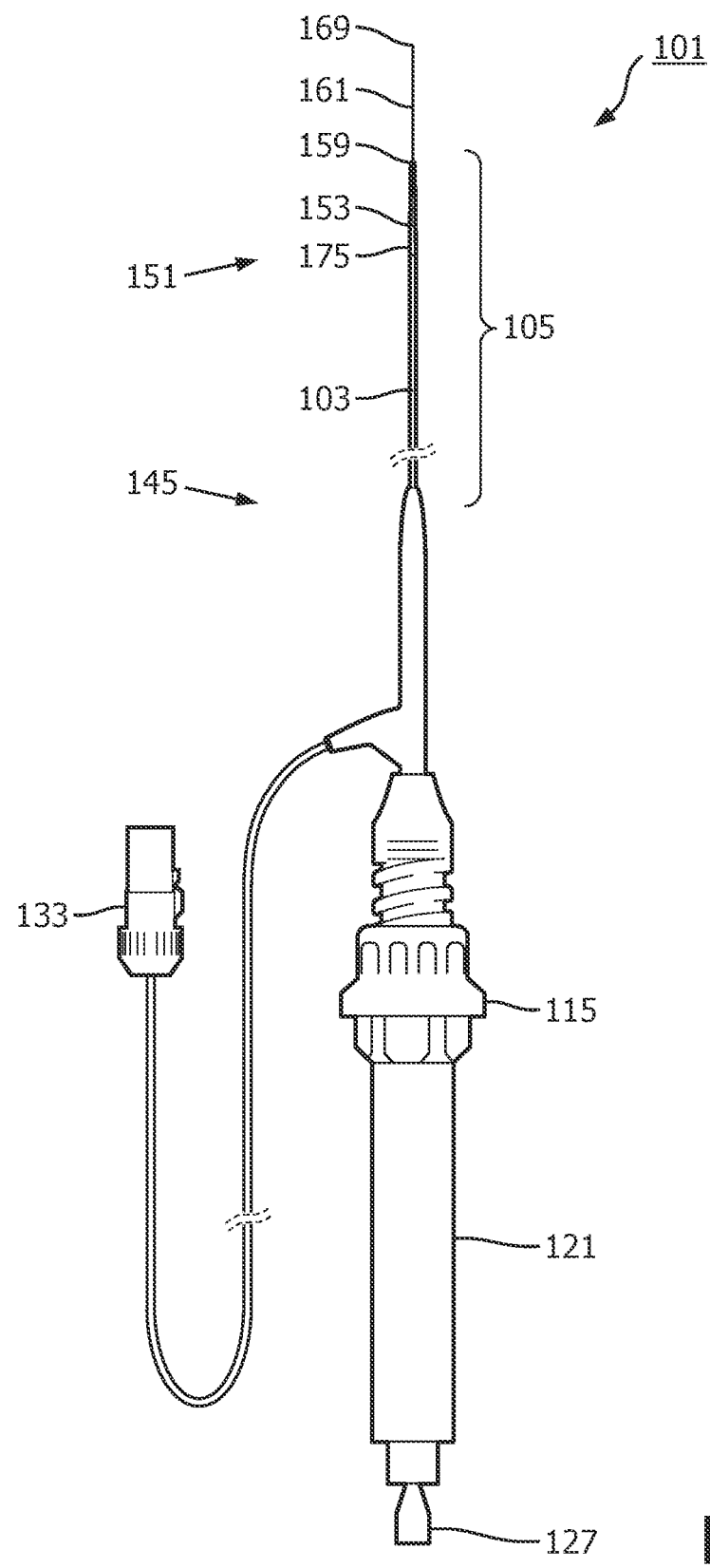
FIG. 1 shows an apparatus for crossing a CTO.

FIG. 1 shows an apparatus 101 for crossing a CTO. Apparatus 101 includes a catheter 103 with an extended body 105 configured for insertion into a vessel of a patient. An intravascular imaging device 175 is disposed on a distal portion 151 of the extended body 105. At a distal end of extended body 105 is an exit port 159. A crossing member 161 is disposed within a lumen 153 in the catheter and configured to be pushed out of the exit port 159 and extend away from the distal end 151 of the extended body, the crossing member comprising a tip 169 configured to cross through the CTO within a true lumen of the vessel.

Apparatus 101 includes a handle member 121 with a locking ring 115. Locking ring 115 can be used to limit or control a distance of extension of crossing member 161. Plug 133 connects imaging transducer 175 to an imaging base station. At a base of handle 121 is lumen access port 127 to access lumen 153.

Any suitable imaging modality may be provided by the imaging device 175 such as, for example, optical coherence tomography, optic-acoustical imaging, ultrasound, capacitive micro ultrasonic transducers (cMUT), piezo micro ultrasonic transducers (pMUT), or any others. In a preferred embodiment, the imaging device 175 operates via intravascular ultrasound (IVUS) using, for example, one or a plurality of cMUTs, pMUTs, or a combination thereof.

The imaging device 175 may use phased-array IVUS device or rotational IVUS. IVUS imaging provides a tool for assessing tissue of the human body from within to determine the need for treatment, to guide an intervention, or to assess its effectiveness. Where intravascular imaging device 175 uses IVUS, the catheter 103 including one or more IVUS transducer is introduced into the vessel and guided to the area to be imaged. The transducers emit and then receive backscattered ultrasonic energy in order to create an image of the vessel of interest. Ultrasonic waves are partially reflected by discontinuities arising from tissue structures (such as the various layers of the vessel wall) and other features of interest. Echoes from the reflected waves are received by the transducer and passed along to an IVUS imaging system. The imaging system processes the received ultrasound echoes to produce a 360-degree, three-dimensional image of the vessel where the device is placed. IVUS imaging devices suitable for modification for use with the invention are described in U.S. Pat. Nos. 4,794,931; 5,000,185; 5,313,949; 5,243,988; 5,353,798; 4,951,677; 4,841,977; 5,373,849; 5,176,141; 5,240,003; 5,375,602; 5,373,845; 5,453,575; 5,368,037; 5,183,048; 5,167,233; 4,917,097; and 5,135,486, each incorporated by reference.

For a typical rotational IVUS device, a single ultrasound transducer element is located at the tip of a flexible driveshaft that spins inside a plastic sheath inserted into the vessel of interest. The transducer element is oriented such that the ultrasound beam propagates generally perpendicular to the axis of the catheter 103. A fluid-filled sheath may protect the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In contrast, solid-state IVUS devices carry a transducer complex that includes an array of ultrasound transducers distributed around the circumference of the device connected to a set of transducer controllers. The transducer controllers select transducer sets for transmitting an ultrasound pulse and for receiving the echo signal. By stepping through a sequence of transmit and receive sets, the solid-state IVUS system can synthesize the effect of a mechanically scanned transducer element but without moving parts. The same transducer elements can be used to acquire different types of intravascular data. The different types of intravascular data are acquired based on different manners of operation of the transducer elements. The solid-state scanner can be wired directly to the imaging system with a simple electrical cable and a standard detachable electrical connector.

The transducer subassembly can include either a single transducer or an array. The transducer elements can be used to acquire different types of intravascular data, such as flow data, motion data and structural image data. For example, the different types of intravascular data are acquired based on different manners of operation of the transducer elements. For example, in a gray-scale imaging mode, the transducer elements transmit in a certain sequence one gray-scale IVUS image. Methods for constructing IVUS images are well-known in the art, and are described, for example in U.S. Pat. Nos. 8,187,191; 7,074,188; 6,200,268, each incorporated by reference. The imaging system allows one image (or frame) of flow data to be acquired. Methods and processes for acquiring different types of intravascular data, including operation of the transducer elements in the different modes (e.g., gray-scale imaging mode, flow imaging mode, etc.) consistent with the present invention are further described in U.S. Pat. No. 7,914,458 to Hossack; U.S. Pat. No. 7,846,101 to Eberle; U.S. Pat. No. 7,226,417 to Eberle; U.S. Pat. No. 6,049,958 to Eberle; and U.S. Pat. No. 5,846,205 to Curley; U.S. Pat. No. 5,921,931 to O'Donnell; and U.S. Pub. 2013/0303907 to Corl, each incorporated by reference. Commercially available software for operating an IVUS catheter in flow mode and displaying flow data is CHROMAFLOW (IVUS fluid flow display software offered by the Volcano Corporation).

In certain embodiments, the imaging device is an OCT device. OCT systems and methods are generally described in U.S. Pat. Nos. 8,108,030; 8,049,900; 7,929,148; 7,853,316; 7,711,413; U.S. Pub. 2011/0152771; U.S. Pub. 2010/0220334; U.S. Pub. 2009/0043191; U.S. Pub. 2008/0291463; U.S. Pub. 2008/0180683; U.S. Pub. 2012/0224751; U.S. Pub. 2012/0136259; U.S. Pub. 2012/0013914; U.S. Pub. 2011/0152771; and U.S. Pub. 2009/0046295, each incorporated by reference.

Imaging device 175 is used to capture an intravascular image and a practitioner can inspect that image to verify that a distal portion of the device 101 is not too close to a vessel wall and thus that extending crossing member 161 out from the device 101 will not damage the vessel wall.

Figure 2:
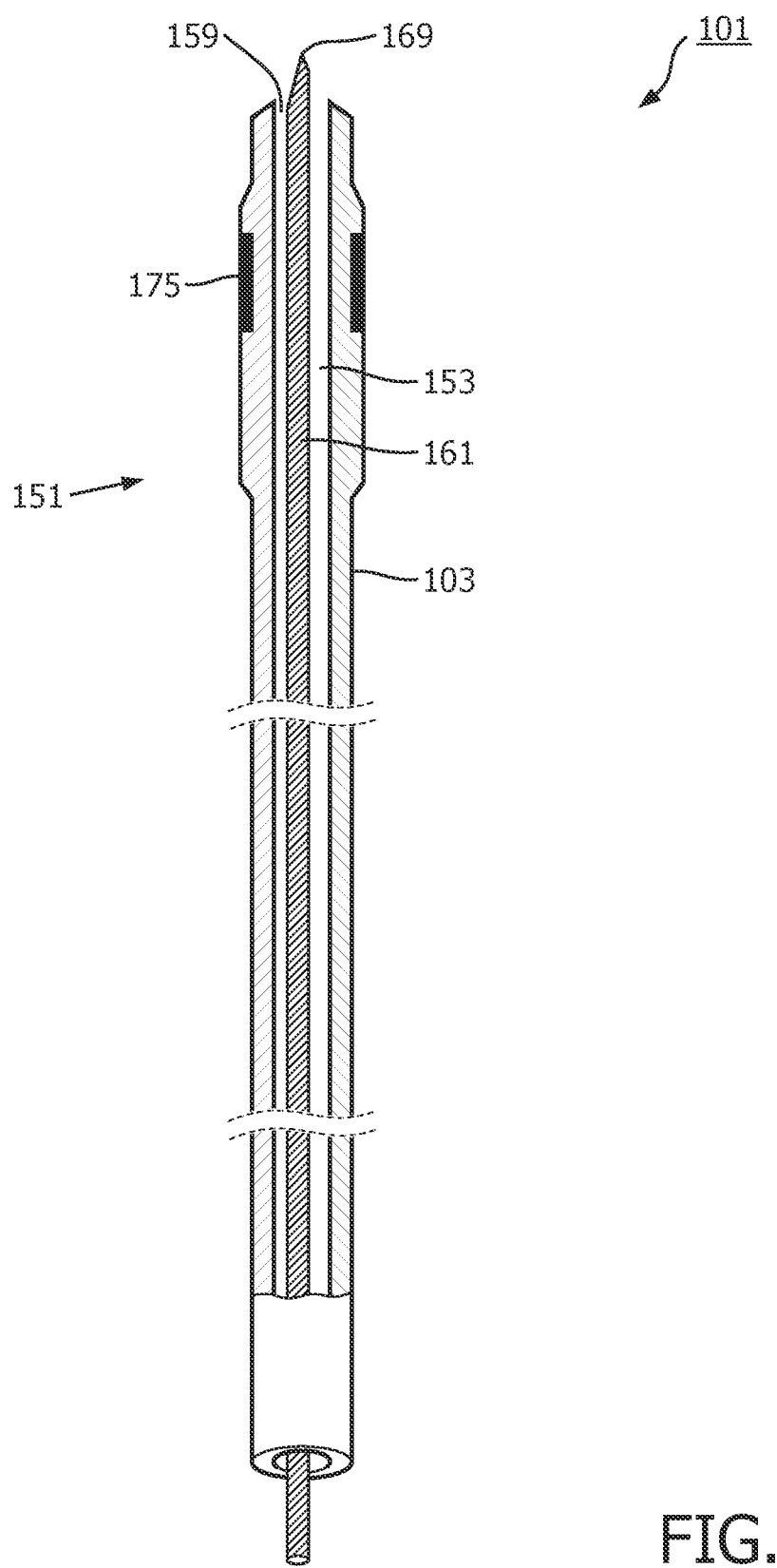
FIG. 2 illustrates a lumen in an over-the-wire configuration.

FIG. 2 illustrates the lumen 153 extending throughout a length of the catheter in an over-the-wire configuration. The crossing member 161 is depicted extending through the lumen 153 in the catheter 103 and configured to be pushed out of the exit port 159.

Preferably, in the extended body 105 of catheter 103, the proximal portions of the extended body 105 will typically be very flexible and suitable for introduction over a guidewire to a target site within the vasculature. As shown in FIGS. 1 & 2, catheter 103 exhibits an "over-the-wire" construction whereby lumen 153 extends fully through the catheter body. As discussed below with respect to FIGS. 3 & 4, devices of the invention may further include "rapid exchange" constructions whereby a guidewire channel extends only through a distal portion of the catheter body. In other cases, it may be possible to provide a fixed or integral coil tip or guidewire tip on the distal portion of the catheter or even dispense with the guidewire entirely. For convenience of illustration, guidewires will not be shown in all embodiments, but it should be appreciated that they can be incorporated into any of these embodiments.

Catheter bodies intended for intravascular introduction will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French. Catheter bodies will typically be composed of an organic polymer that is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, often the coronary arteries, by conventional techniques.

The crossing member 161 is included and configured to pierce through occlusions. In preferred embodiments, the crossing member 161 is forward-facing (directly towards the CTO) rather than side-facing (e.g., as described in U.S. Provisional Patent Application No. 62/024,520, filed Jul. 15, 2014, as well as any publication of any application claiming the benefit of that Provisional Application). The crossing member 161 of apparatus 101 preferably extends from a lumen 153 that defines an over-the-wire construction. In some embodiments, the invention provides a device that also includes a separate guidewire lumen.

Figure 3:
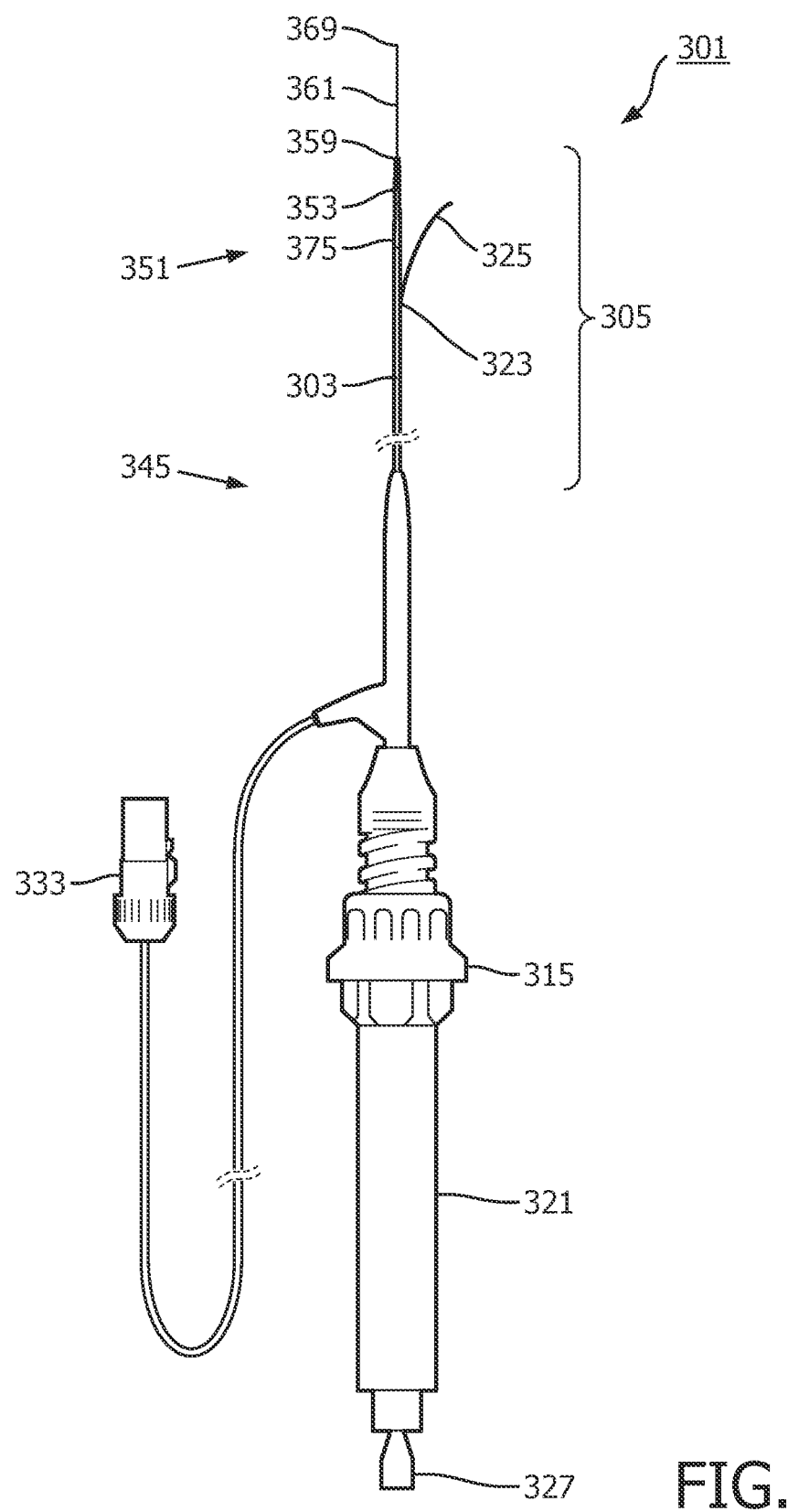
FIG. 3 shows an apparatus with a separate guidewire lumen.

FIG. 3 shows an apparatus 301 for crossing a CTO that includes a separate guidewire lumen 323. Apparatus 301 includes a catheter 303 with an extended body 305 configured for insertion into a vessel of a patient. An intravascular imaging device 375 is disposed on a distal portion 351 of the extended body 305. At a distal end of extended body 305 is an exit port 359. A crossing member 361 is disposed within a primary lumen 353 in the catheter and configured to be pushed out of the exit port 359 and extend away from the distal end 351 of the extended body, the crossing member comprising a tip 369 configured to cross through the CTO within a true lumen of the vessel. A guidewire 325 extends from guidewire lumen 323. As drawn in FIG. 3, guidewire lumen 313 has an exit port proximal to the intravascular imaging device 375. However, the exit port may be distal to the device 375 without departing from the scope of the invention.

Apparatus 301 includes a handle member 321 with a locking ring 315. Plug 333 connects imaging transducer 375 to an imaging base station. At a base of handle 321 is a primary lumen access port 327 to access primary lumen 353.

Figure 4:
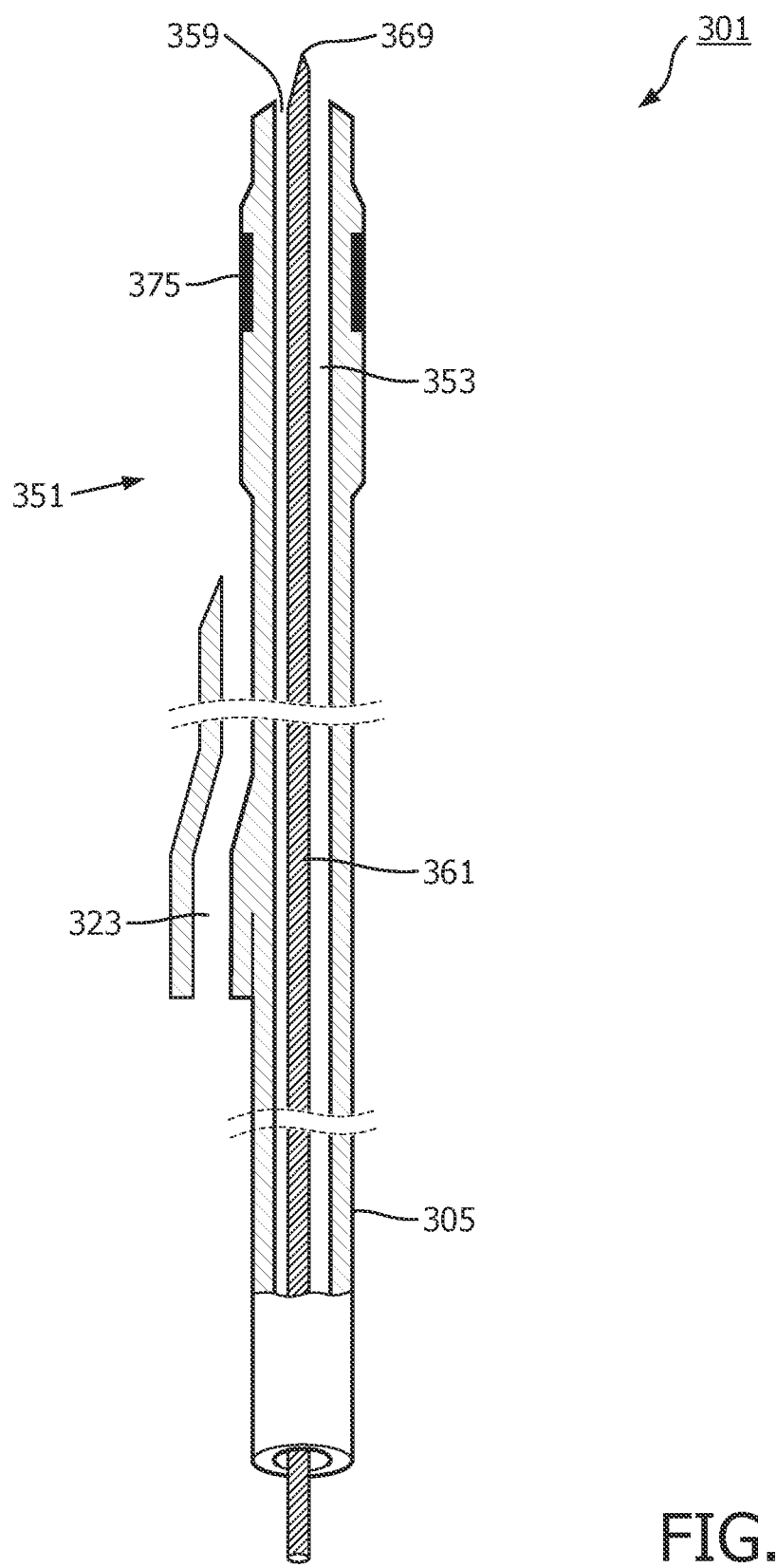
FIG. 4 shows an arrangement of the lumen and the guidewire lumen.

FIG. 4 shows an arrangement of the guidewire lumen 323 within the device 301. The guidewire lumen 323 extends along a portion of the length of the catheter in a rapid exchange configuration. Inclusion of a separate guidewire lumen 323 can aid a practitioner in performing complex procedures such as guiding a separate balloon catheter to a CTO after crossing member 361 has made a preliminary crossing through the CTO.

An apparatus for crossing a CTO includes a crossing member with ample stiffness for being pushed through a CTO. In general, it may be preferable to include a crossing member with greater stiffness than the stiffness of a sub-intimal re-entry catheter, such as the subintimal re-entry catheter illustrated in U.S. Pub. 2013/0072957 to Anderson, which pierces through tissue. The crossing member of an apparatus of the invention may be made stiffer through the use of stiff materials such as certain alloys or steels, through the inclusion of certain structures such as braiding or lateral ridges, through thickness, or a combination thereof. A thickness of the crossing member can be described by its flexural modulus. In certain embodiments, a crossing member has a flexural modulus of at least 20 GPa, which increases its ability to pierce through the occlusion (rather than tissue). Flexural modulus can be measured as described in Harrison, 2011, Guidewire stiffness: what's in a name?, J Endovasc Ther 18(6):797-801. The flexural modulus Ef, given in giga-pascals (GPa), is represented by Equation 1.

$$Ef = (L^3 F)/(48 \times I \times D) \quad \text{(Equation 1)}$$

where L is the distance between supports, F is the force, D is the deflection, and I is the second moment of area of the wire about the neutral plane.

For a guidewire with a circular cross section, I is determined by Equation 2.

$$I = (Pi \times d^4)/(64) \quad \text{(Equation 2)}$$

where d is the guidewire diameter and Pi is approximately 3.14. An apparatus of the invention includes a crossing member configured to pierce through a CTO and an intravascular imaging catheter for carrying the crossing member to the CTO. A crossing member may be configured to pierce through a CTO by making it stiff, by giving it a CTO-piercing tip, or both. Additionally, an apparatus of the invention may include a pushing mechanism for pushing the crossing member through the CTO. For example, the apparatus may include a spring-loaded mechanism that can be used to generate the force needed to push the crossing member through the occlusion.

Figure 5:
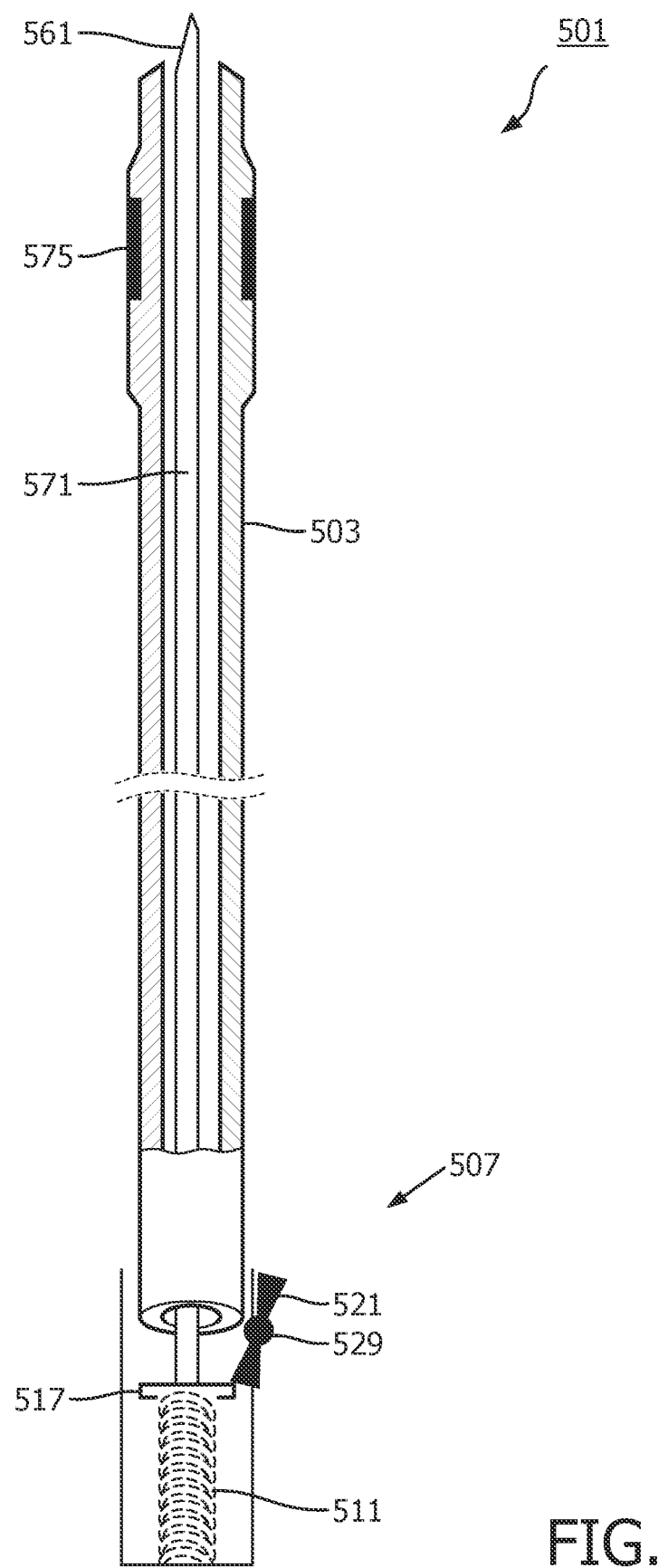
FIG. 5 shows a crossing apparatus with a spring mechanism.

FIG. 5 shows an apparatus 501 for crossing a CTO that includes spring mechanism 507 configured to exert force on the crossing member to push the crossing member through the CTO. Apparatus 501 includes catheter 503 housing a forward-exit crossing member 561 that can be extended out of the catheter 503. Apparatus 501 also includes an intravascular imaging device 575 such as a phase-array IVUS transducer. Mechanism 507 includes one or more springs 511 engaged within the device behind a pushable surface 517 that, when pushed, tends to push a crossing member 571 forward out of the device. Additionally, mechanism 507 includes a catch 521 mounted on a pivot 529 (and catch 521 may itself be spring-loaded or biased towards the engaged position). Catch 521 provides a détente mechanism inside of the apparatus as well as a trigger handle on the outside of the device such that depressing the handle releases the spring 511 urging the crossing member 571 forward.

In some embodiments, an apparatus of the invention includes, e.g., as a terminus of a crossing member, a needle that is predisposed to pierce in a forward direction towards the lumen and avoid accidental vessel wall puncture. To aid in accomplishing CTO puncture and avoiding vessel damage, an apparatus of the invention may include a mechanism to bias the body of the apparatus away from a vessel wall (e.g., towards a center of the vessel). The biasing mechanism may be provided by one or more self-centering feature such as a balloon or expandable funnel braid. Other features that may center an apparatus in a vessel are described in U.S. patent application Ser. No. 14/201,070, filed Mar. 7, 2014, and any patent or publication of that application.

Figure 6:
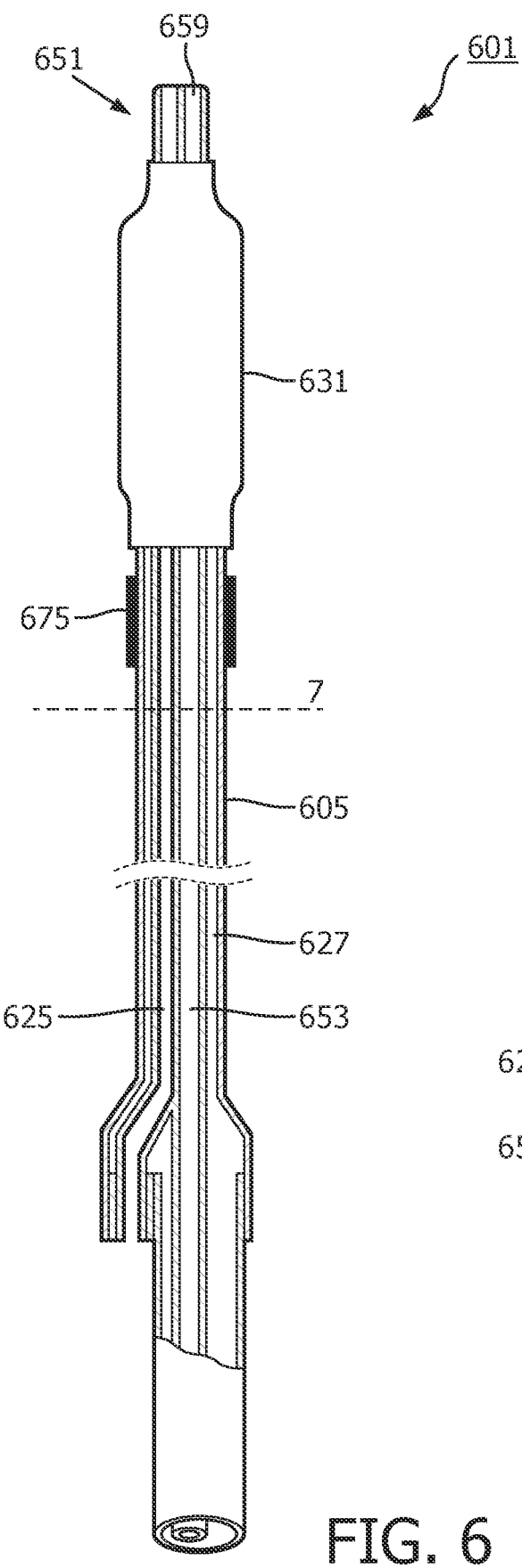
FIG. 6 illustrates a crossing apparatus with a self-centering balloon.

FIG. 6 illustrates an apparatus 601 for crossing a CTO that includes a self-centering feature provided by a balloon 631. Inflation lumen 627 extends down a length of catheter body 605 and is in fluid communication with balloon 631. Apparatus 601 includes a catheter with an extended body 605 configured for insertion into a vessel of a patient. An intravascular imaging device 675 is disposed on a distal portion 651 of the extended body 605. In the depicted embodiment, imaging device 675 is just proximal to balloon 631, but it may be just distal or in any other convenient location. At a distal end of extended body 605 is an exit port 659. A crossing member may be disposed within a lumen 653 in the catheter and configured to be pushed out of the exit port 359 and extend away from the distal end 151 of the extended body, the crossing member having a tip configured to cross through the CTO within a true lumen of the vessel. Devices suitable for modification for use with the invention are shown in U.S. Pat. No. 6,458,099 to Dutta.

Figure 7:
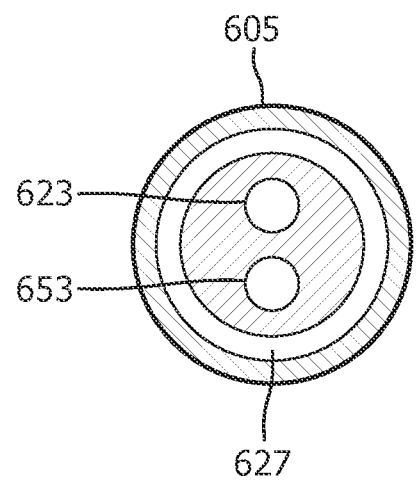
FIG. 7 is a cross-section through an apparatus showing lumens therein.

FIG. 7 is a cross-section through the extended body of apparatus 601 along the line marked "7" to show an arrangement of the lumens therein. Inflation lumen 631 is circumferentially disposed around the body 605, and the lumen 653 as well as guidewire lumen 625 extend therethrough. Inflation lumen 627 may be used to deliver a fluid (e.g., water, saline, a gas) to the balloon 631 thereby deploying the balloon 631 within the vessel and biasing the exit port 659 away from a wall of the vessel.

Figure 8:
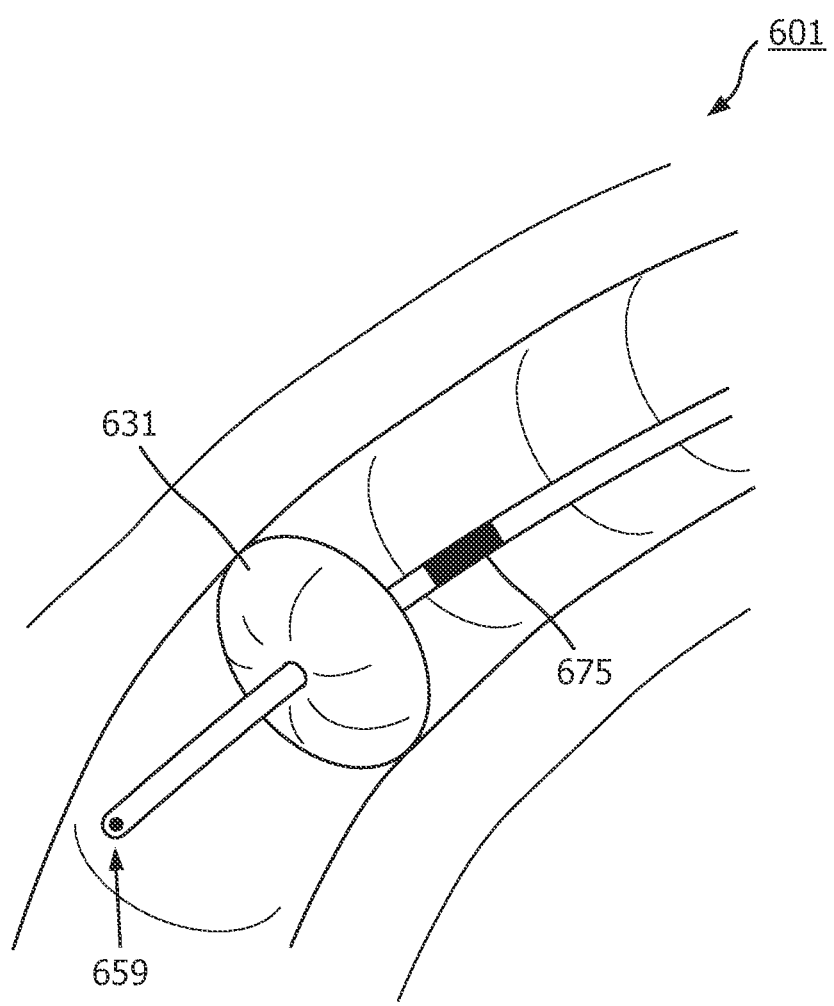
FIG. 8 illustrate the balloon apparatus with the balloon deployed.

FIG. 8 illustrate apparatus 601 with the centering balloon 631 deployed. Since the balloon 631 biases the imaging device 675 away from the wall of the vessel, the imaging device may be able to produce a better image of the vessel that be easier to interpret during a procedure. Since the balloon 631 biases the exit port 659, and consequently any crossing member extending therefrom, away from the walls of the vessel, a practitioner has a tool for avoiding trauma to the vessel walls. Thus a balloon 631 is one self-centering mechanism that may be useful with a device of the invention, although others may be used additionally or alternatively.

Figure 9:
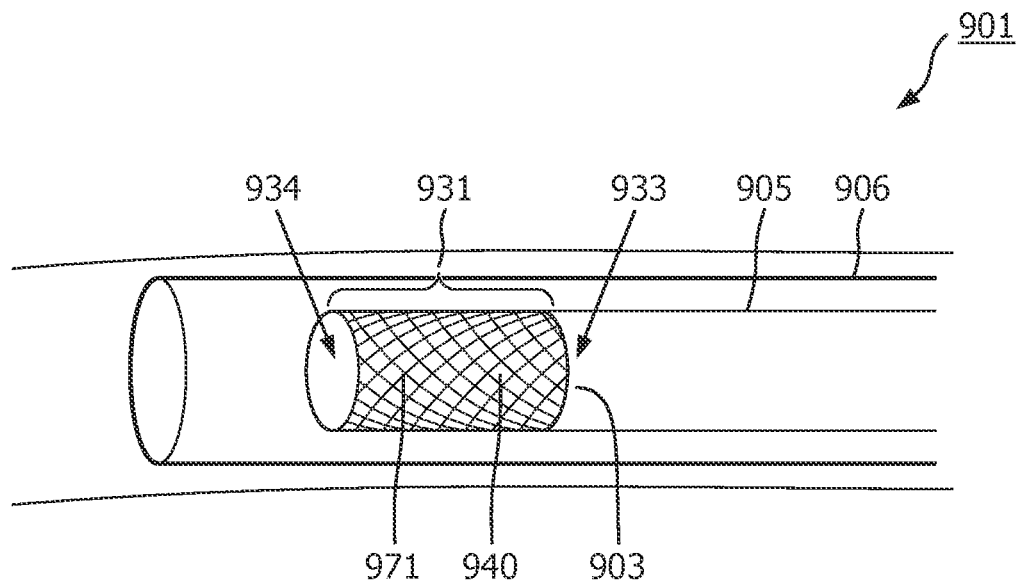
FIG. 9 illustrates a crossing apparatus with a self-centering feature.

FIG. 9 illustrates an apparatus 901 for crossing a CTO that includes a self-centering feature that uses an expandable funnel braid 931. Funnel 931 is preferably connected to an extended body 905 of a catheter 903 of apparatus 901 at a base 903 of funnel 901, which may also include an outer sheath 906 slidably disposed over the catheter body 905.

In this embodiment, the funnel 931 is configured from a flexible support material 971. Preferably, the support material 971 is configured as a plurality of braided support elements such as wires with a diameter of about 0.004. These support elements are preferably configured from NiTi. However, they may also be configured from other suitable materials. The proximal end 933 of the funnel 931 has a fixed diameter and is attached to the distal portion of an extended body of a catheter of apparatus 901 (e.g., of any of the embodiments of FIG. 1, FIG. 2, etc.). The funnel braid can be made from shape memory alloys, like nitinol.

In certain embodiments, the support material 971 may be covered with a funnel sheath 940. The funnel sheath 40 is preferably about 0.003 inches in thickness and covers and partially makes up the funnel 931. Preferably the funnel sheath 940 is configured from expanded polytetrafluoroethylene (ePTFE), urethane, silicon, or another suitable polymer material. The funnel sheath 940 is preferably configured by rolling back ePTFE, or another suitable material, over itself to form multiple layers.

The distal end 934 of the funnel 931 is contained by an outer sheath 906 over the guide catheter 905. Once the catheter 903 is positioned in the vessel, the outer sheath 906 may be removed, thereby allowing the distal end 934 of the funnel 931 to expand.

Figure 10:
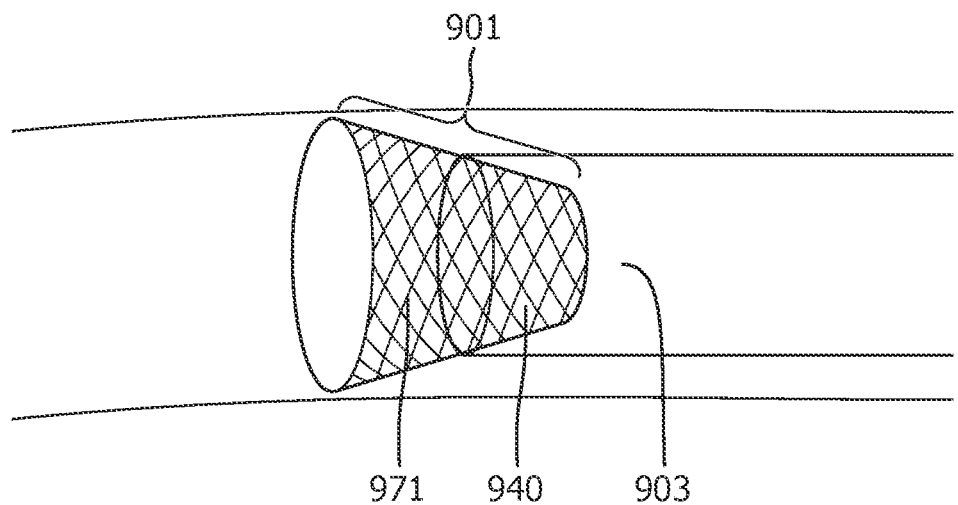
FIG. 10 shows the expandable funnel braid deployed.

FIG. 10 illustrate apparatus 901 with the expandable funnel braid deployed. The distal end 934 of the funnel 931 may then be compressed when the outer sheath 906 is positioned back over the distal end 934 of the funnel 931, thereby avoiding damage to the vessel during the retrieval of the apparatus 901. Centering mechanisms that use a funnel braid are discussed in U.S. Pub. 2005/0159770 to Divani. Centering mechanisms are a potentially helpful tool in a catheter with a crossing member or needle for true lumen CTO crossing.

Another feature that may be included is a specialized needle tip configured to be pushed through a CTO, e.g., at a distal end of a crossing member. The piercing tip can be fashioned in a number of ways to facilitate direct crossing of the occlusion. The tip can be needle-tipped, blunt-tipped, or drill-tipped for example. The tip can also be configured with RF-emitting capabilities. In other instances, a waterjet can be used to help blast through the CTO. The tip can also be configured with a cutting balloon. Once the tip is somewhat through the occlusion, the cutting balloon can then be expanded to eliminate the CTO.

FIG. 11 illustrates a tip 1169 that defines a sharpened needle point. A CTO can sometimes have a very hard, dense fibrous cap and it may be found that a sharpened, or even beveled, tip is preferred to pierce through the fibrous cap.

One insight of the invention is that the fibrous cap of a CTO is sometimes naturally traversed by microchannels that guide the crossing member in an unintended and undesired direction. The existence of microchannels is known. See Carlino, 2008, CTO recanalization by intraocclusion injection of contrast: The microchannel technique, Cath and Cardio Interventions 71(1):20-16. However, without being bound by any particular mechanism it may be found that microchannels actually mis-guide the crossing wire or needle such that when the needle is pushed forward it follows the microchannel until it makes contact with a vessel wall. It may be found that a blunt or preferably even a burred tip has an improved ability to drive through a fibrous cap without getting unnecessarily diverted by a microchannel.

FIG. 12 illustrates a tip 1269 that is intermediate between pointed and blunt. The tip of intermediate bluntness may present the best compromise for piercing ability of CTO cap material while being minimally traumatic upon incidental contact with a vessel wall. Additionally, the blunted portion of the end may accommodate a needle lumen (see FIG. 26).

FIG. 13 illustrates a tip 1369 that wherein the tip defines a blunt end. The blunted morphology may provide a good ability to plow through a CTO without getting diverted by a microchannel.

FIG. 14 illustrates a tip 1469 that includes one or more burs 1404. Burrs 1404 can be included that add additional roughness and present additional traumatic edges to the tip 1469. Particularly when used in conjunction with a centering device, a tip 1469 with burs 1404 may provide an excellent ability to effectively saw or tear through the fibrous cap of a CTO. Additionally or alternatively a crossing member can be configured or operated to drill through a CTO.

Figures 15, 16:
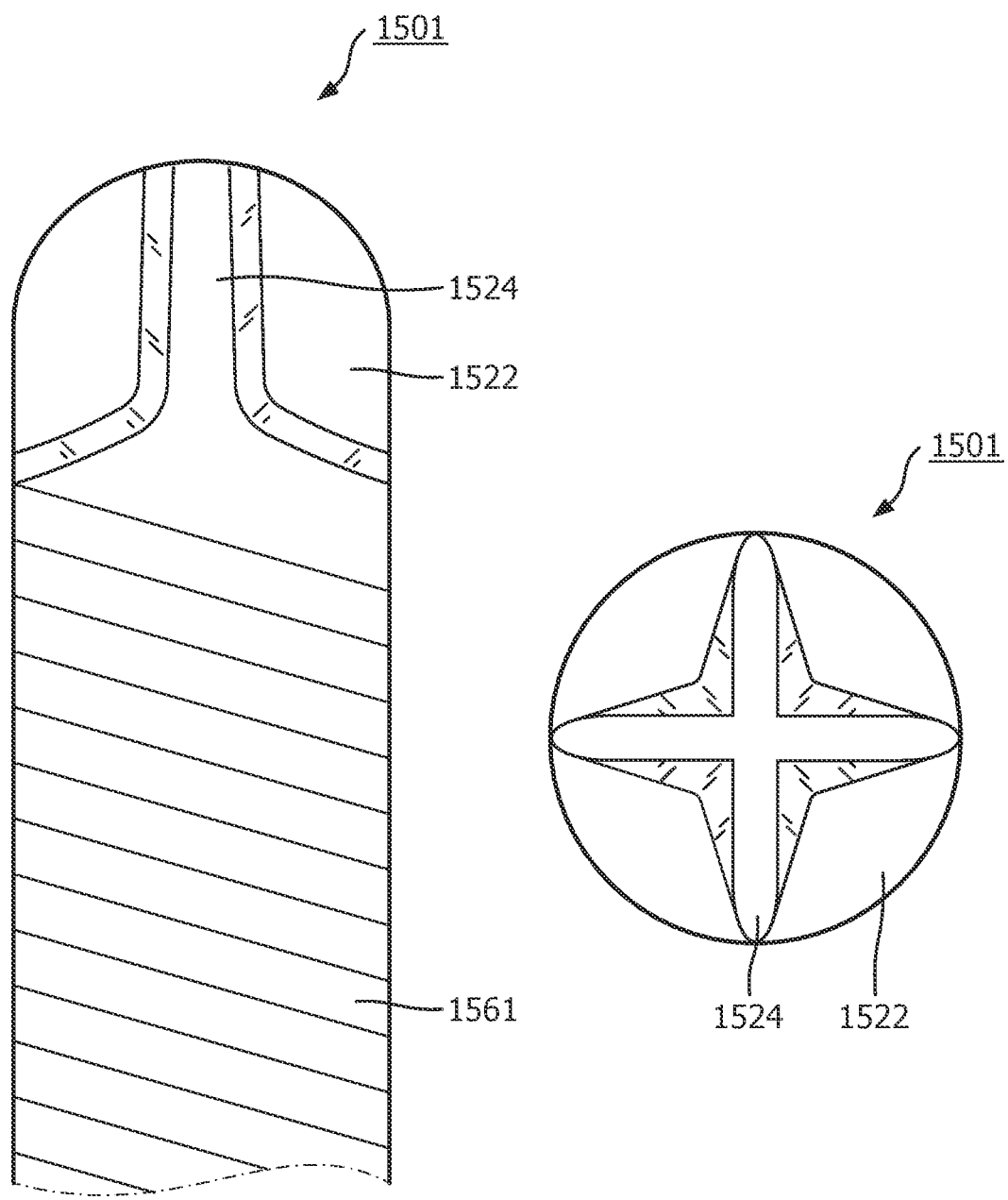
FIG. 15 illustrates a tip that defines a drill mechanism.
FIG. 16 is a head-on view of the drilling mechanism.

FIG. 15 illustrates a tip of a crossing member 1561 that defines a drill mechanism 1501. Preferably, a proximal end of crossing member 1561 is attached to a torquer (manual or motorized). The crossing member 1561 may be removable from the torquer. The torquer may be similar to a conventional electric drill, with crossing member 1561 serving a function similar to that of a drill bit. The torquer may be provided by a device such as is described in U.S. patent application Ser. No. 14/204,314, filed Mar. 11, 2014, and any patent or publication of that application.

Preferably, crossing member 1561 is removable from torquer and may be advanced through a patient's vasculature prior to attaching the guidewire to the torquer. Once crossing member 1561 is at the CTO, a proximal end may be inserted into the torquer and retained using, for example, a clamp, a chuck, or a collet. The torquer may include a rotator motor, which may then be activated to cause the entire crossing member 1561 to rotate. The rotation of drilling mechanism 1501 causes the portion to bore through the obstruction, allowing the crossing member 1561 to be extended beyond the obstruction.

FIG. 16 is a head-on view of drilling mechanism 1501. Drilling mechanism 1501 is sized to bore an opening through a CTO and may be approximately 1 to 10 millimeters in length. Drilling mechanism 1501 preferably has at least two cutting elements. In the present embodiment, drilling mechanism 1501 includes longitudinal flutes 1522. The flutes are thin, blade-like structures that, when the guidewire is rotated, act as cutting elements to allow drilling mechanism 1501 to bore through an obstruction such as a chronic total occlusion. The crossing member may be rotated manually or using a mechanical rotator such as is described above. The drilling mechanism 1501 may be formed using, for example, a hydraulic press with a fixture shaped to press indentations into the distal end of crossing member 1561. One skilled in the art will appreciate that other methods, including metal cutting, electric discharge machining (EDM) and metal injection molding (MIM), may be used to form structures into the distal tip of the guidewire.

Drilling mechanism 1501 may use any suitable material such as a stainless steel, nitinol or age-hardenable nickel-cobalt-chromium-molybdenum alloy wire and includes an elongate body portion of crossing member 1561 and drilling mechanism 1501. The drilling portion is symmetrical and has a plurality of cutting elements comprising flutes framed by areas of relief. The drilling portion is sized to bore an opening having a diameter substantially the same as that of the elongate body portion. U.S. Pub. 2006/0184186 to Noone reports a drilling wire for treating chronic total occlusions.

In some embodiments, the invention provides devices and methods for RF energy delivery.

Figure 17:
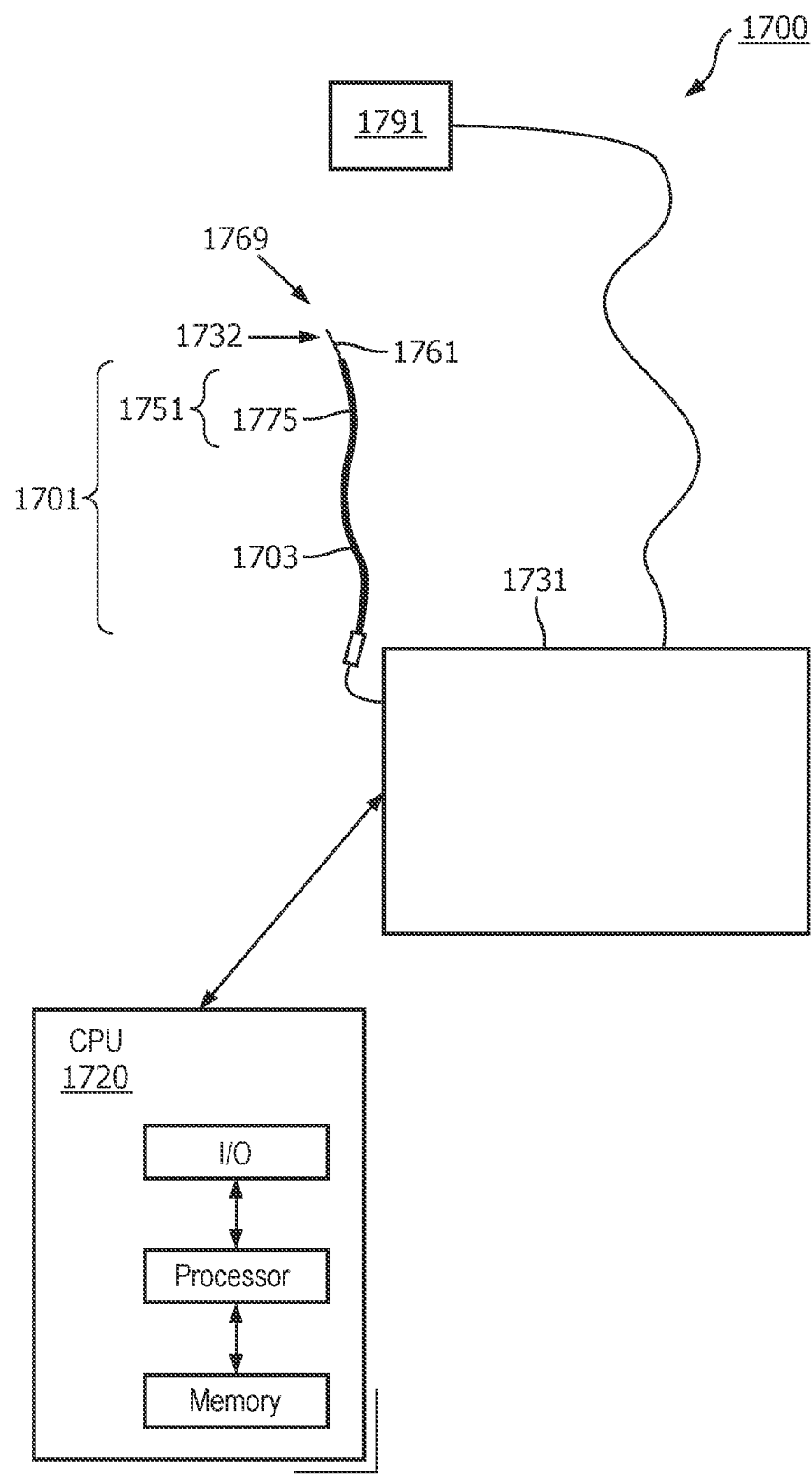
FIG. 17 diagrams a system configured to deliver RF energy to disrupt a CTO.

FIG. 17 diagrams a system 1700 with an apparatus 1701 for crossing a CTO that includes a catheter 1703 comprising a crossing member 1761 having a tip 1769 configured to deliver RF energy to disrupt the CTO. Preferably the tip 1769 includes at least one electrode 1732, e.g., a spark erosion electrode by which obstructive plaque can be ablated in conjunction with an IVUS imaging system by which the anatomy of the artery and obstruction may be visualized. The objective of system 1700 is to provide the practitioner with information as to the location and the characteristics of the CTO, coupled with the ability to provide a controlled spark erosion of the occlusive materials.

Wires for the ultrasound signals and a high-voltage wire to transmit RF energy to the active electrode extend through the catheter 1703 and crossing member 1761, respectively. See discussion in U.S. Pat. No. 6,394,956. System 1700 may be used for crossing a CTO with simultaneous IVUS imaging in combination with RF ablation A distal end 1751 of the catheter 1703 is configured to be inserted into a patient and is constructed to be navigable through the patient's vasculature to advance the distal tip of the catheter to the intended treatment site. The catheter 1703 includes an imaging device 1775 and a crossing member 1761 with a distal tip 1769 that carries an electrode 1732 for delivering energy to an obstructed portion of the vessel.

The system includes an electronics module 1731 that includes circuitry and software for generating signals for operating the ultrasonic system and for receiving and processing the signals from resulting ultrasound echoes, as well as for generating the RF ablation signal. The central processing unit 1720 constructs the images from the received ultrasound signals and displays the image on a monitor. The image is generated on demand. The image may be caused to fade after a predetermined time as a reminder to the operator to refresh the image. The central processing unit 1720 may comprise a laptop or desktop computer or a dedicated embedded processor. Separate cables run from the catheter to the electronics module 1731 and carry ultrasound signals and RF energy.

In certain embodiments, catheter 1705 and more particularly crossing member 1761 may be rotated and advanced entirely under the manual control of the physician. Similarly, the initiation of the ablation pulse is determined by the physician independently of any direct connection with the catheter or the system for sensing catheter rotation. It should be understood, however, that reference to "manual" with respect to control over the application of ablation energy may include any arrangement by which the physician, based on judgment as to the proper location of the ablation electrode, initiates the ablation sequence. Thus, "manual" operation may include a variety of arrangements, including, mechanically controlled switches (e.g., a foot switch, or a voice-operated control) or other means by which the physician can trigger the ablation cycle.

The tip 1769 may be fabricated from a suitable thermoset material having high temperature capability sufficient to withstand temperatures that may be developed by the RF ablation sparking. Materials such as a castable epoxy resin, or a castable ceramic may be used. Alternately, the body of the tip may be machined from a suitable ceramic such as alumina zirconia. The tip 1769 may be formed to define a distally-facing leading surface to facilitate its advancement through the patient's vasculature. The tip may have a diameter or cross-sectional dimension of the order of about 1.5 mm. In the embodiment shown in FIG. 17, the tip 1769 is monopolar and includes an RF ablation electrode 1732 and the system also includes a counter-electrode 1791 that remains outside of a patient's body.

The electrode 1732 may be gold plated, photo-etched stainless steel or machined platinum. These materials provide good electrical conductivity for ablating tissue and are radiopaque to facilitate visualization of the tip under fluoroscopy. The ultrasound transducer may be made from lead zirconate titanate (PZT) or polyvinylidene di-fluoride (PVDF). The transducer may be between 250 and 650 micrometers in diameter. The crossing member 1761 carries conductors by which the electrical signals from the RF ablation antenna 1732 and are transmitted between the distal tip and the electronics module 1731.

The catheter shaft 1705 carries conductors by which the electrical signals the transducer 34 are transmitted between the distal tip and the electronics module 1731. Apparatus and methods for intravascular ultrasound imaging and for crossing severe vascular occlusions with RF ablation are discussed in U.S. Pat. No. 8,480,593 to Magnin.

In other aspects and embodiments, devices of the invention may include fluid jets to aid in cutting through a CTO.

Figure 18:
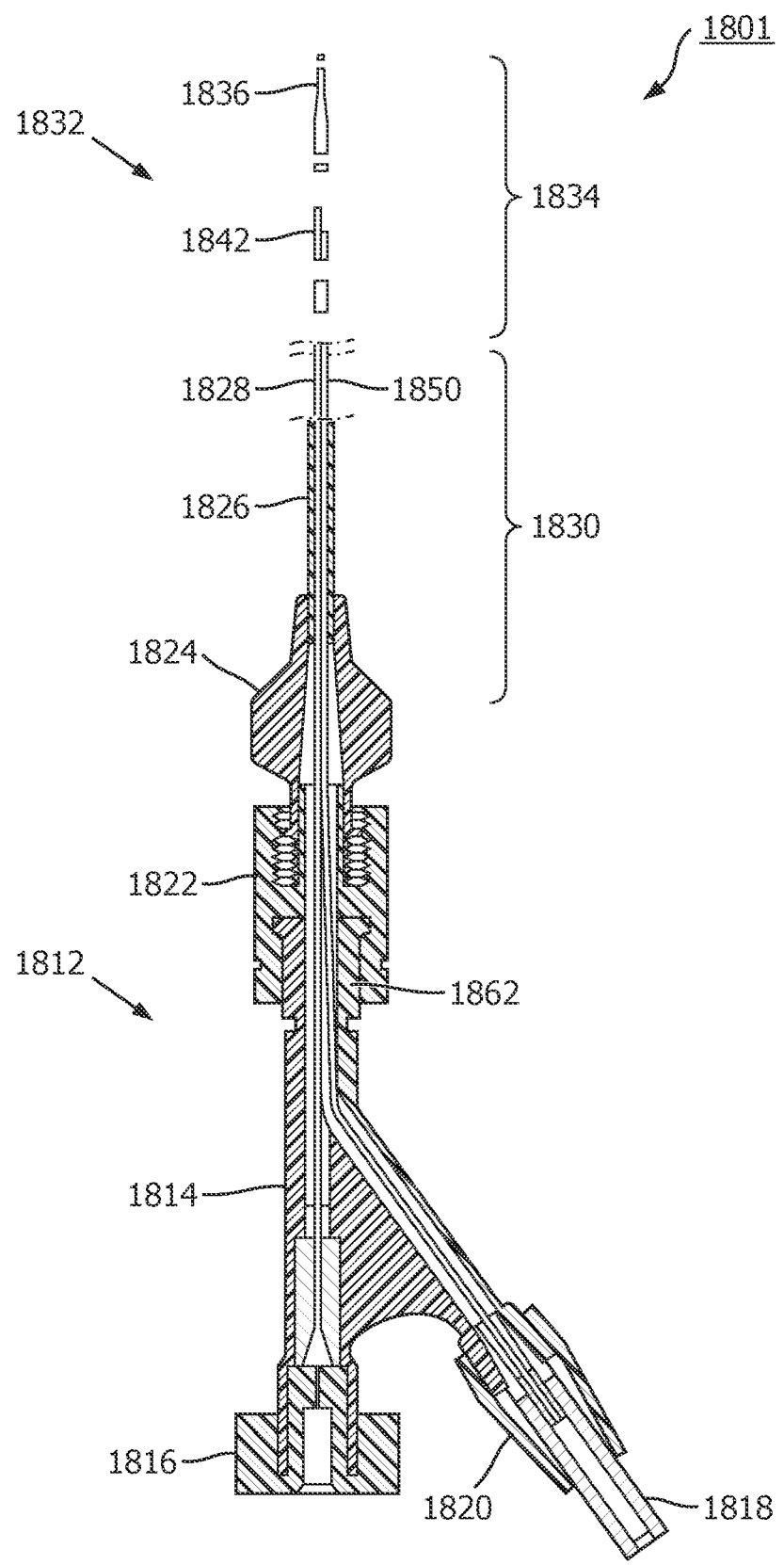
FIG. 18 is cross-sectional view through a crossing apparatus with a fluid jet.

FIG. 18 is cross-sectional view through an apparatus 1801 for crossing a CTO that includes a fluid jet as part of the crossing catheter to deliver fluid to cut through the CTO. Apparatus 1801 includes a manifold 1812 having a central body 1814, a hemostasis valve 1816, a high pressure connector 1818, a Luer fitting 1820, a Luer connector 1822, a winged Luer fitting 1824, and a strain relief tube 1826. Manifold 1812 may be used in conjunction with an IVUS catheter handle such as handle 121 shown in FIG. 1. Extending from the interior of the manifold 1812 and through the strain relief tube 1826 in a distal direction is a torqueable and flexible (4 French) proximal catheter tube 1828, preferably of a polyether block amide such as the material sold under the trademark PEBAX, which, in general, delineates the greater portion of a low pressure cavity 1830. Device 1801 further includes a distal catheter tube at a distal portion.

Figure 19:
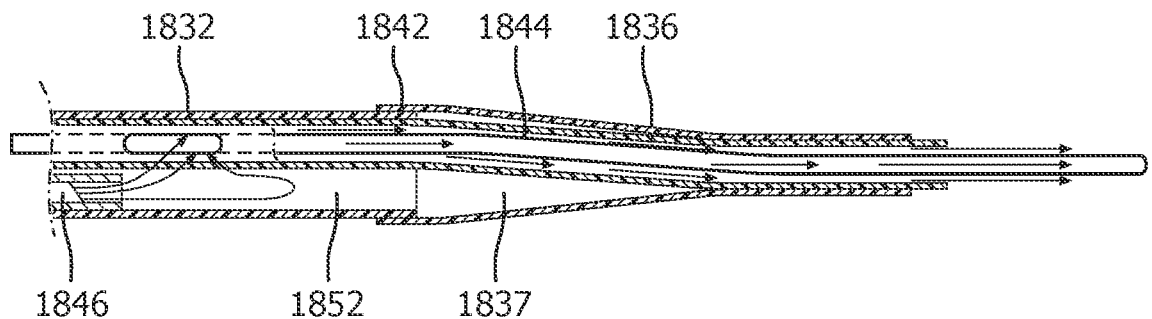
FIG. 19 is a close-up cross-section of a distal end of a crossing apparatus with a fluid jet.

FIG. 19 shows a close-up cross-sectional view of a torqueable and short reduced diameter flexible and shapeable low profile (3 French) distal catheter tube 1832, preferably polyether block amide, which, in general, delineates the greater portion of a high pressure cavity 1834 extending along the distal catheter tube 1832 and along a flexible tapered tip 1836 having a lumen attached to the distal end of the distal catheter tube 1832. Marker bands may be located over and about the opposing ends of the tapered tip 1836.

Preferably, one marker band is securingly aligned over the overlapping coaxial junction of the proximal end of the tapered tip 1836 and the distal end of the distal catheter tube 1832, and another marker band is securingly aligned over the overlapping coaxial junction of the distal end of the tapered tip 1836 and the distal end of the guidewire tube 1842. The proximal ends of a guidewire tube 1842 having a lumen 1844 and a high pressure tube 1846 having a lumen 1848 are aligned and secured within the manifold 1812. The central and greater portions of the guidewire tube 1842 and the high pressure tube 1846 are aligned in a lumen 1850 of the proximal catheter tube 1828 and also extend to align in the proximal portion of the lumen 1852 of the distal catheter tube 1832 where such a proximal portion of the lumen 1852 is proximal to an adhesive plug seal. The distally located shorter portions of the guidewire tube 1842 and the high pressure tube 1846 are aligned and extend within the distal portion of the lumen 1852 of the distal catheter tube 1832, where such a distal portion of the lumen 1852 is distal to the adhesive plug seal 1854, and are secured therein by the use of the adhesive plug seal 1854 in the distal catheter tube 1832. In addition, the distal end of the guidewire tube 1842 extends further into and is secured in the lumen 1837 of the tapered tip 1836. The low pressure cavity 1830 (FIG. 18) is associated generally with the proximal catheter tube 1828 and the high pressure cavity 1834 is generally associated with the lumen 1852 of the distal catheter tube 1832 and with the lumen 1837 of the flexible tapered tip 1836.

The manifold 1812 includes connected and communicating passageways and cavities located along and about the central body 1814 including a central passageway therethrough. A small radius section extends through a distal tubular body 1862 ending in an annular connector flange. Threads are located about the proximal exterior portion of the cavity body at the proximal region of the manifold 1812 for accommodation of internal threads of the hemostasis nut 1816. Methods of fabricating apparatus 1801 are described in U.S. Pub. 2008/0312672 and in U.S. Pat. No. 7,226,433.

Together, the illustrated components form a manifold low pressure region through manifold 1812. The manifold low pressure region is connected to and in direct communication with the low pressure cavity 1830 of the proximal catheter tube 1828. The low pressure cavity 1830 includes the section of the lumen 1850 of the proximal catheter tube 1828 extending distally from the proximal end of the proximal catheter tube 1828 to the point of an intersection with the proximal end of the distal catheter tube 1832 and the associated section of the lumen 1852 of the distal catheter tube 1832 and also includes the section from the point of intersection of the proximal catheter tube 1828.

The guidewire tube 1842 extends generally parallel to the high pressure tube 1846. The proximal end of the guidewire tube 1842 extends into the tapered bore of the guidewire tubular adapter in manifold 1812. The guidewire tube 1842 extends through the lumen 1850 of the proximal catheter tube 1828 and into the proximal end of the lumen 1852 of the distal catheter tube 1832, i.e., the low pressure cavity 1830. The guidewire tube 1842 then extends through the adhesive plug seal 1854 and continues into the portion of the lumen 1852 of the distal catheter tube 1832 and further within the lumen 1837 of the tapered tip 1836 to finally terminate and be secured within the distal end of the tapered tip 1836, i.e., the guidewire tube 1842 extends into and resides in the high pressure cavity 1834.

Figure 20:
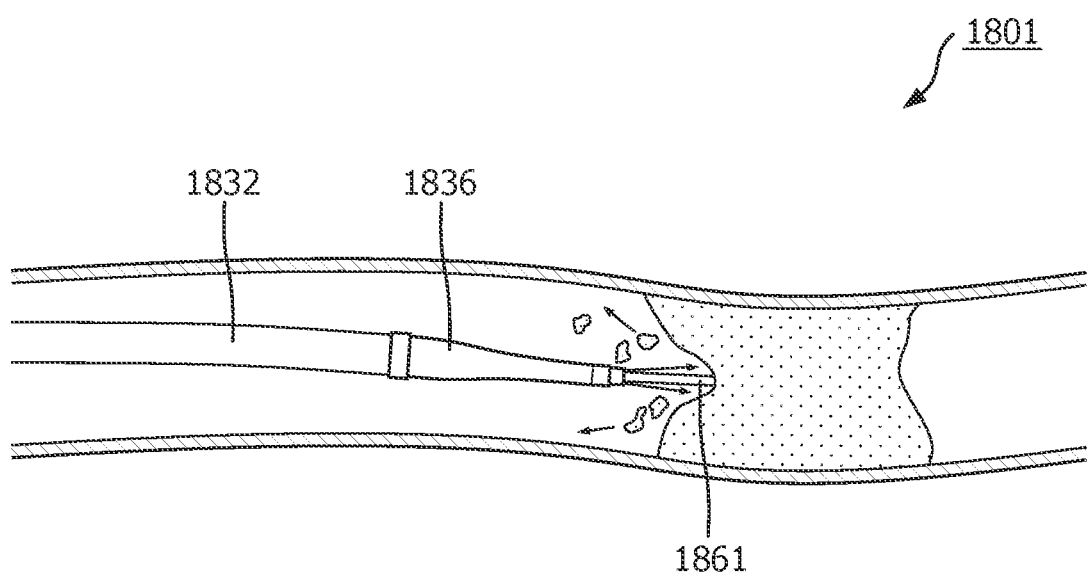
FIG. 20 shows a fluid jet in use in crossing a CTO.

FIG. 20 shows the distal end of the distal catheter tube 1832 and the flexible tapered tip 1836 of the forwardly directed fluid jet crossing apparatus 1801 aligned within a patient's vessel having a CTO. The distal end of a crossing member 1861 is positioned in close proximity to or in intimate contact with the CTO. The crossing member 1861 is aligned along the interior length of the forwardly directed fluid jet crossing catheter apparatus 1801. More precisely, the crossing member 1861 is aligned within the manifold 1812 and closely associated components thereof, indirectly within the proximal catheter tube 1828 and the distal catheter tube 1832, indirectly within the low pressure cavity 1830 and high pressure cavity 1834, indirectly within the lumen 1837 of the tapered tip 1836, and directly within the lumen 1844 of the guidewire tube 1842. The tapered tip 1836 is shown positioned at or near the CTO. A fluid jet stream is directed along the crossing member 1861 toward the CTO in order to form and provide a path through the CTO, thereby forming a crossing therethrough. The fluid jet stream provides a moderate velocity cylindrical flow along the outer surface of the crossing member 1861, as also shown in FIG. 20, or can provide an increased volume cylindrical flow fluid jet stream when the distal end of the crossing member 1861 is repositioned.

In certain aspects and embodiments, devices and methods of the invention are provided to aid in breaking up or destroying a CTO. For example, once an initial path has been formed and provided through the CTO, a therapeutic device or agent may be inserted or introduced into that path to further relieve the patient of uncomfortable symptoms. In certain embodiments, an apparatus of the invention includes a cutting a balloon that can be inflated within a part of a CTO. The cutting balloon has one or more cutting edges on a surface there of, and the cutting edges help break up the CTO by, for example, cutting up the hard fibrous cap.

Figure 21:
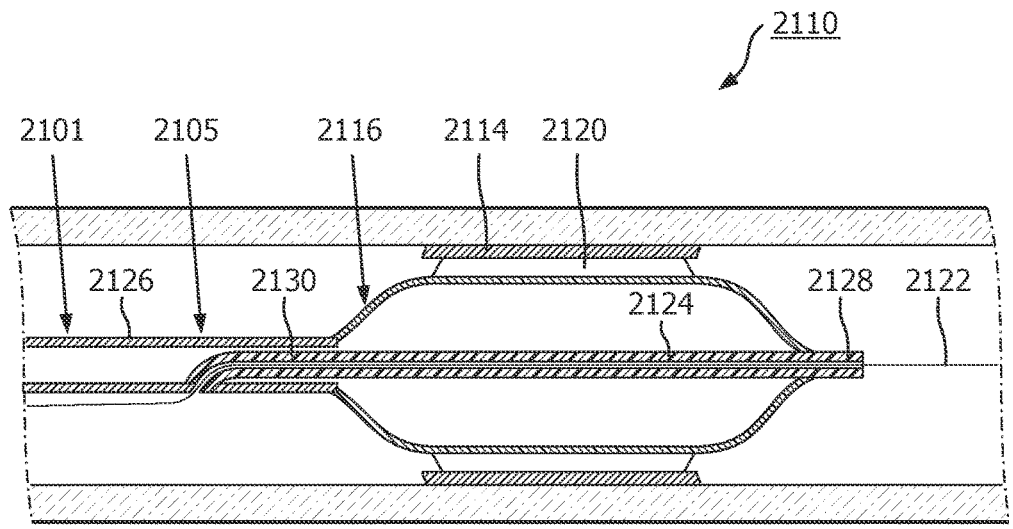
FIG. 21 is a partial cross-section side view of a crossing apparatus with a cutting balloon.

FIG. 21 is a partial cross-sectional side view of an apparatus 2110 for crossing a CTO and that uses a cutting balloon 2116. Apparatus 2110 is configured to be introduced into a blood vessel 2112 and positioned adjacent an intravascular lesion 2114. Catheter 2110 includes a balloon 2116 coupled to a catheter shaft 2118. One or more cutting members or blades 2120 may be coupled to balloon 2116. In general, catheter 2110 may be advanced over a guidewire 2122, through the vasculature, to a target area. Balloon 2116 can then be inflated to expand lesion 2114, and cutting members 2120 may cut lesion 2114. The target area may be within any suitable peripheral or cardiac vessel lumen location.

Cutting members 2120 may vary in number, position, and arrangement about balloon 2116. For example, catheter 2110 may include one, two, three, four, five, six, or more cutting members 2120 that are disposed at any position along balloon 2116 and in a regular, irregular, or any other suitable pattern. In general, cutting members 2120 may be configured to have enhanced flexibility.

Balloon 2116 may be made from typical angioplasty balloon materials including polymers such as polyethylene terephthalate (PET), polyetherimide (PEI), polyethylene (PE), elastomeric polyamides, block polyamide/ethers, polyether block amide (PEBA, for example, available under the trade name PEBAX), silicones, Marlex high-density polyethylene, Marlex low-density polyethylene, polyetheretherketone (PEEK), polyimide (PI), polyphenylene sulfide (PPS), polyphenylene oxide (PPO), or other suitable materials or mixtures, combinations, or copolymers thereof.

Balloon 2116 may be configured so that it includes one or more "wings" or wing-shaped regions when balloon 2116 is deflated. These wings may appear as a plurality of alternating inward and outward radial deflections in balloon 2116 when balloon 2116 is deflated. These wings may be desirable for a number of reasons. For example, by including balloon 2116 with wings, balloon 2116 may have more predictable and consistent re-folding characteristics. Additionally, the wings may be configured so that cutting members 2120 can be positioned at the inward-most positions of the deflated balloon 2116. This arrangement allows cutting members 2120 to be positioned more closely to shaft 2118 when balloon 2116 is deflated. Accordingly, cutting members 2120 can be moved away from the vessel walls where they might otherwise result in contact and, possibly, damage to healthy tissue during movement of catheter 2110 within a body lumen. Additionally, alternating the wings and cutting members 2120 as well as positioning cutting members 2120 relatively close to shaft 2118 may allow the wings to fold over and cover cutting members 2120 when balloon 2116 is deflated. Again, this feature may reduce the exposure of cutting members 2120 to the blood vessel.

Shaft 2118 may be a catheter shaft, similar to typical catheter shafts. For example, shaft 2118 may include an inner tubular member 2124 and outer tubular member 2126. Tubular members 2124/26 may be manufactured from a number of different materials. For example, tubular members 2124/26 may be made of metals, metal alloys, polymers, metal-polymer composites or any other suitable materials. Some examples of suitable metals and metal alloys include stainless steel, nickel-titanium alloy such as linear-elastic or super-elastic Nitinol, nickel-chromium alloy, or other alloy or suitable material. Some examples of suitable polymers include those described above in relation to balloon 2116. Of course, any other polymer or other suitable material including ceramics may be used without departing from the spirit of the invention. The materials used to manufacture inner tubular member 2124 may be the same as or be different from the materials used to manufacture outer tubular member 2126. Those materials listed herein may also be used for manufacturing other components of catheter 2110 including cutting members 2120.

Tubular members 2124 may be arranged in any appropriate way. For example, in some embodiments inner tubular member 2124 can be disposed coaxially within outer tubular member 2126. According to these embodiments, inner member 2124 and outer tubular member 2126 may or may not be secured to one another along the general longitudinal axis of shaft 2118. Alternatively, inner tubular member 2124 may follow the inner wall or otherwise be disposed adjacent the inner wall of outer tubular member 2126 Inner tubular member 2124 includes an inner lumen 2128. In at least some embodiments, inner lumen 2128 is a needle lumen. Needle lumen 2128 can be used to bring a needle to a CTO for crossing the CTO. Needle lumen 2128 preferably extends along essentially the entire length of catheter shaft 2118 so that catheter 2110 resembles a traditional "over-the-wire" catheter. Additionally, the apparatus 2101 may include a guidewire lumen extending along only a portion of shaft 2118 so that catheter 2110 resembles "single-operator-exchange" or "rapid-exchange" catheters.

Shaft 2118 may also include an inflation lumen 2130 that may be used, for example, to transport inflation media to and from balloon 2116. The location and position of inflation lumen 2130 may vary. For example, when outer tubular member 2126 is disposed over inner tubular member 2124, inflation lumen 2130 may be defined within the space between tubular members.

Balloon 2116 may be coupled to catheter shaft 2118 in any of a number of suitable ways. For example, balloon 2116 may be adhesively or thermally bonded to shaft 2118.

In addition to some of the structures described above, shaft 2118 also includes at least one intravascular imaging device (e.g., as described with respect to FIG. 1 or FIG. 3) and at least one crossing member extending through a lumen therethrough. Additionally shaft 2118 may include other features such as any of the other features described herein or other ones that are typically associated with catheter shafts. For example, shaft 2118 may include a radiopaque marker coupled thereto that may aid a user in determining the location of catheter 2110 within the vasculature. In addition, catheter 2110 may include a folding spring (not shown) coupled to balloon 2116, for example, adjacent proximal waist 2132, which may further help in balloon folding and refolding. A description of a suitable folding spring can be found in U.S. Pat. No. 6,425,882, which is incorporated herein by reference.

As described above, cutting members 2120 may be configured to have increased flexibility. Flexibility may be conferred by the method by which cutting members 2120 are joined to balloon 2116.

Figure 22:
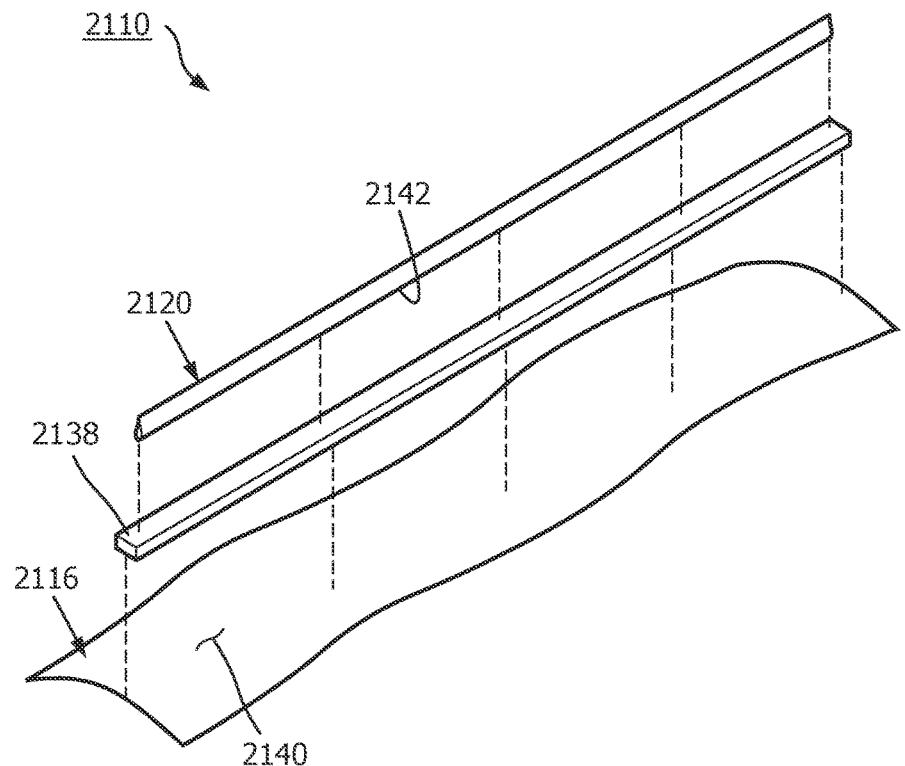
FIG. 22 illustrates a construction of a cutting member on a cutting balloon.

FIG. 22 illustrates a construction of a cutting member 2120 according to certain embodiments. A flexible joining member 2138 may be coupled to cutting member 2120 and to balloon 2116. Joining member 2138 may be formed from a generally flexible or soft material that allows the interface between cutting member 2120 and balloon 2116 to be somewhat elastic or pliable. For example, joining member 2138 may be manufactured from a low durometer polyurethane or any other suitable material (including any of the polymers and other materials disclosed herein). Accordingly, cutting member 2120 may be able to move laterally about eight degrees or less. In addition, different portions of cutting member 2120 may be able to bend or flex, while other portions remain essentially unchanged. Joining member 2138 can be attached to and disposed between cutting member 2120 and balloon 2116. For example, joining member 2138 can be attached to an outer surface 2140 of balloon 2116 and to a base 2142 of the cutting member 2120. The attachment of joining member 2138 with cutting member 2120 and balloon 2116 may be achieved in any appropriate manner, such as by adhesive bonding, casting, thermal bonding, mechanically connecting, welding, brazing, and the like, or in any other suitable way. The attachment means need not be the same for the attachment between cutting member 2120 and joining member 2138 as the means used to attach balloon 2116 and joining member 2138.

Other features described herein may be included in an apparatus of the invention.

In certain aspects and embodiments, the invention provides an apparatus 2301 for crossing a CTO that includes a deflectable tip mechanism to steer the tip towards an area of interest. Safety can be enhanced through the use of a deflectable or steerable tip. The deflectable tip mechanism can steer the tip towards an area of interest (i.e., the plaque) rather than towards the vessel wall.

Figure 23:
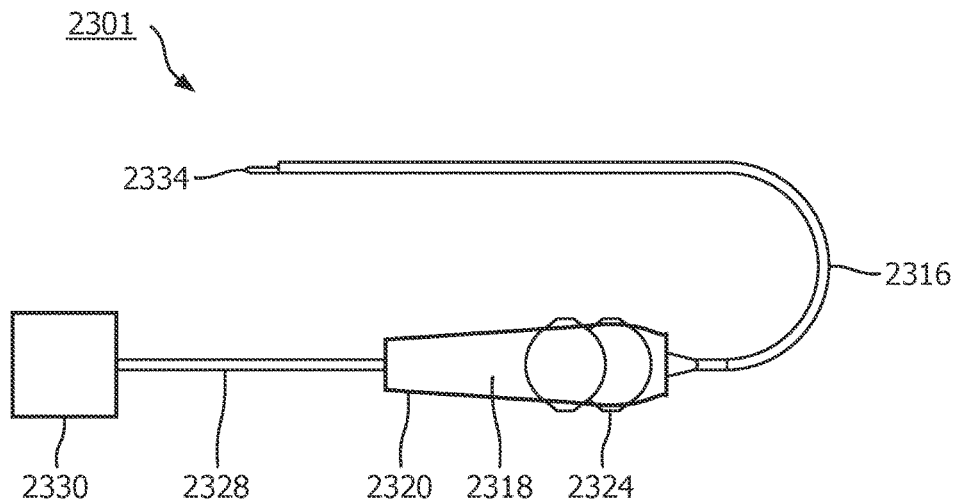
FIG. 23 shows a steerable intravascular imaging apparatus for crossing a CTO.

FIG. 23 shows a steerable intravascular imaging apparatus 2301 for true-lumen crossing of a CTO. Apparatus 2301 includes a catheter body with shaft 2312. The catheter shaft 2312 is a generally flexible elongate member having a distal segment 2314, a proximal segment 2316, and at least one lumen (not shown). The proximal segment 2316 is attached to a handle 2318. The handle 2318 includes, by way of example, a housing 2320, a steering actuator 2324.

The actuator 2324 is manipulated by a user moving an exposed control surface of the actuator 2324 lengthwise along the length of the housing 2320 of the handle 2318. In alternative embodiments, thumb-controlled slider actuators replace the rotating knobs. The distal segment 2314 is, by way of example, 10 cm long. However, an exemplary range for the length of the distal segment 2314 is from 5 cm to 2320 cm. A tip of the distal segment 2314 has a generally smaller diameter than the diameter of the proximal segment 2316 of the catheter shaft. The catheter shaft 2312 is made, by way of example, of engineered nylon (polyether block amide) and includes a tube or tubing, alternatively called a catheter tube or catheter tubing that has at least one lumen.

In the illustrative example in FIG. 23, the steering actuator 2324 is accessible (have exposed control surfaces through the housing 2320) on two sides of the handle 2318. A strain relief 2326 protects the catheter shaft 2312 at a point where the catheter shaft proximal segment 2316 meets the handle 2318. A cable 2328 connects the handle 2318 to a connector 2330. The connector 2330, which can be any of many possible configurations, is configured to interconnect with an imaging system for processing, storing, manipulating, and displaying data obtained from signals generated by a sensor mounted at the distal segment 2314 of the catheter shaft 2312. An exemplary catheter steering mechanism is presented in U.S. Pat. No. 5,358,478 to Thompson.

Figure 24:
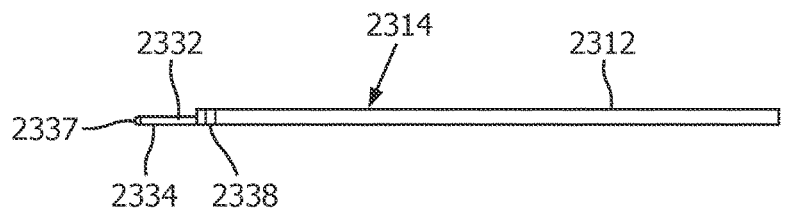
FIG. 24 shows the steerable apparatus in a straight configuration.
Figure 25:
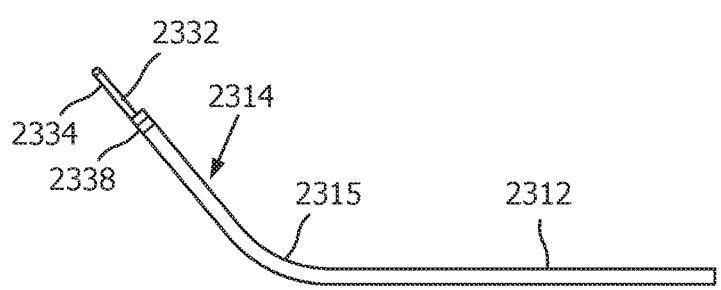
FIG. 25 shows the steerable apparatus in a bent configuration.

FIGS. 24 and 25 illustrate how distal segment 2314 can be steered or deflected. The catheter 2312 is flexed, using the actuator 2324, from a straight configuration as illustrated in FIG. 24 into a flexed steering configuration, as illustrated in FIG. 25. In addition, the catheter 2312's distal segment 2314 is steerable into any number of flexed positions in between the straight configuration of FIG. 24 and the flexed configuration of FIG. 25, and can even be flexed beyond the configuration of FIG. 25. The catheter is capable of flexing past the 90° point in each direction and has an angular range of 0° to 150° from the straight or neutral configuration. The second direction is similar to what has been illustrated in FIG. 25, and it can be appreciated that it is simply the mirror image of the configuration of FIG. 25 illustrated for the first direction.

To affect flexing the distal segment 2314 in the manner described above, the second steering actuator 2324 (e.g., knob) is turned in a first rotational direction with respect to the relatively fixed position handle 2318. Rotating the actuator 2324 in the first direction causes a first steering wire to apply tension to a steering bulkhead 2338 forcing the distal segment 2314 of the catheter shaft 2312 to bend at bending joint 2315 (see, FIG. 24). In order to flex the catheter in the opposite direction, the second steering actuator 2324 is turned in an opposing second rotational direction with respect to the handle 2318. This causes a second steering wire to apply tension to an opposite side of steering bulkhead 2338, forcing the catheter to bend in an opposite direction at the bending joint 2315. The catheter assembly 2310, by way of example, supports bidirectional flexed steering by at least 23150 degrees in each direction from a neutral or straight catheter position. Using the combination of these two steering modes (rotational and flexing) is much more intuitive to the user than a steering mechanism based solely on either rotation or flexing—but not both. In an example of a method for using the catheter assembly 2310 having both rotational and flex steering, a crossing member (such as one shown in FIG. 1 or FIG. 3) is first placed into a desired location of the body. While visualizing the vessel and thus a location of the crossing member within the vessel, such as with ultrasound, the second steering actuator 2324 is adjusted until the catheter orientation is close to the desired orientation.

Cable wires from the connector extend through a proximal orifice. The catheter steering mechanisms and signal wire bundle extend through distal orifice. The lower portion of the thumb and the two smallest fingers comfortably grip the handle at a grip area. The shape of the handle and positioning of the actuators permits easy access for the thumb on the top of the handle and either the index or middle finger on the bottom of the handle to manipulate the steering actuator 2324 while maintaining hold on the grip area of the handle.

In certain embodiments, a lock lever protrude slightly above the outer edges/diameters of the steering actuator 2324. While in the resting locked position shown, the locking mechanisms controlled by the levers do not allow 2324 to be moved, thus maintaining the catheter 2310 in its desired flex state. While a user's thumb manipulates one of the actuator 2324, the associated one of the lock lever is held down slightly by the thumb, releasing the corresponding locking mechanism and allowing the actuator to be moved (e.g., the knob rotates). After the actuator 2324 is moved to the desired position and the thumb is taken off the lock lever, the corresponding lock automatically engages the actuator 2324, holding the actuator 2324 in the desired position until the next time it is to be moved.

Other features described herein may be included in an apparatus of the invention.

In certain aspects and embodiments, the invention provides an apparatus for crossing a CTO that includes a delivery mechanism for injecting drugs through the tip of the crossing member into a cap of the CTO. In some embodiments, the apparatus includes a mechanism for delivering or injecting drugs through the tip of the crossing member into the CTO cap. For example, an apparatus of the invention may include a delivery lumen (e.g., through the crossing member or through the catheter) as a mechanism for injecting agent through the tip of the crossing member into a cap of the CTO. Suitable agents include thrombolytic drugs or an agent to dissolve the CTO such as ethanol.

Figure 26:
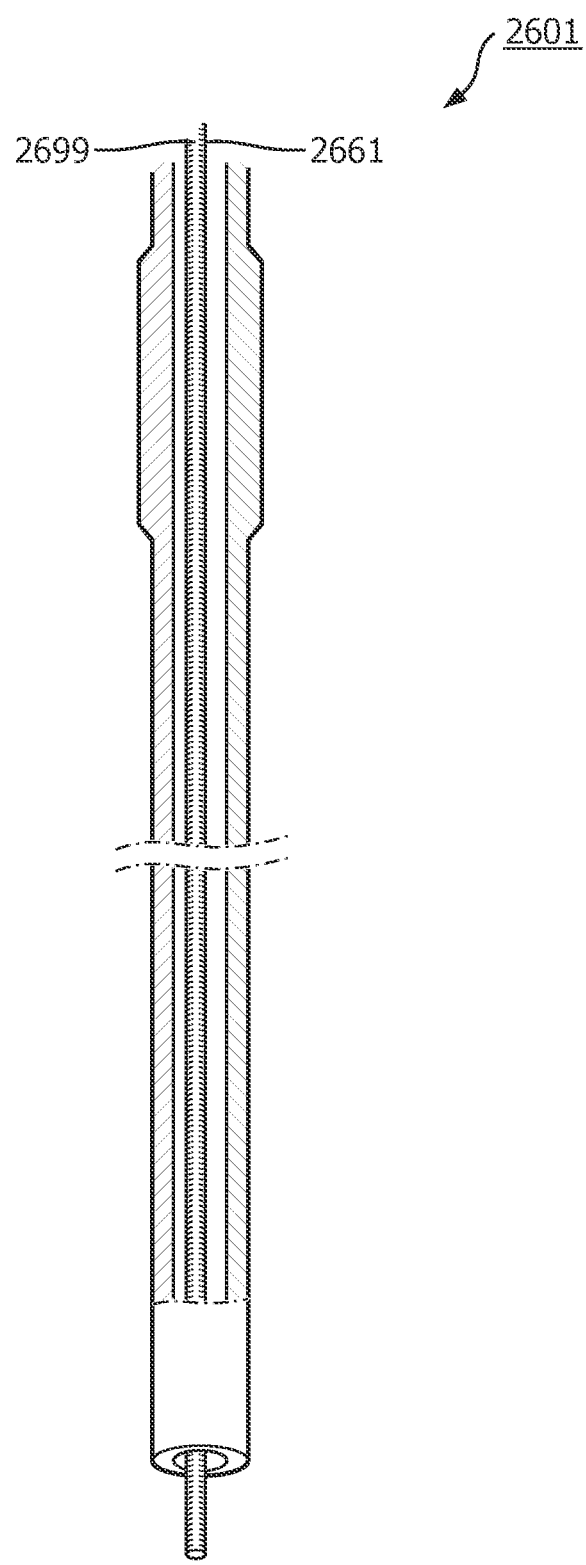
FIG. 26 shows a crossing apparatus with a mechanism for delivering a treatment agent.

FIG. 26 shows an apparatus 2601 for crossing a CTO that includes a delivery mechanism for injecting drugs through the tip of the crossing member 2661 into a cap of the CTO. Crossing member 2661 includes an inner delivery lumen 2699 extending therethrough. The drugs can be used to soften the fibrous cap which consists of fibrin, thrombin, collagen, lipids and calcium. After softening the cap and creating a small channel, then a percutaneous transluminal angioplasty (PTA) balloon may be inserted to open up the channel and form a patent lumen. Another aspect of the drug could be used to prevent restenosis or further calcification from developing.

Figure 27:
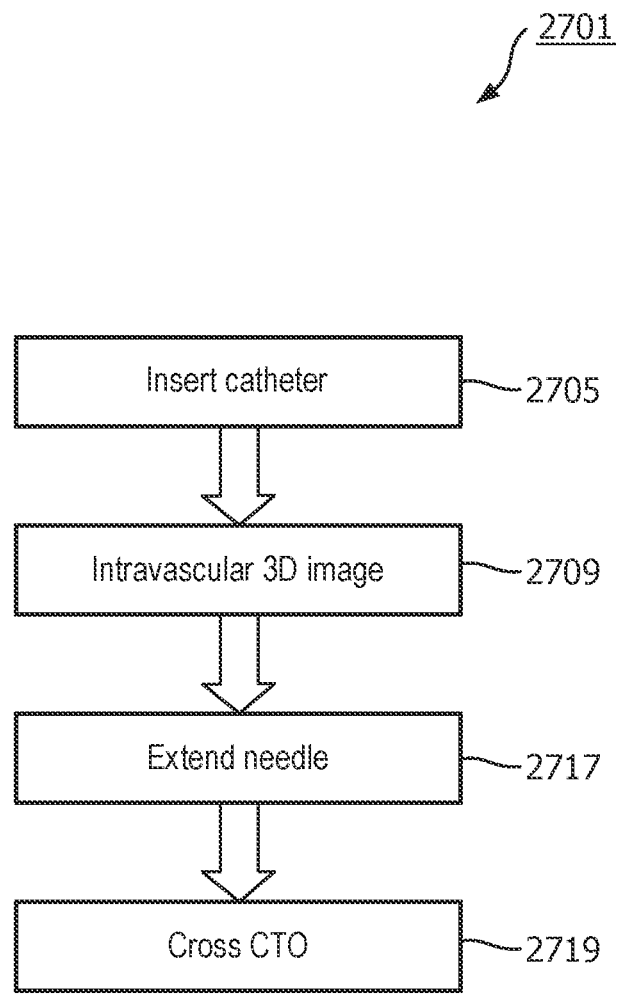
FIG. 27 diagrams of a method of crossing a CTO.

In certain aspects and embodiments, the invention provides a method for crossing a CTO. FIG. 27 shows a diagram of a method 2701 of crossing a CTO. A catheter apparatus such as anyone shown herein is inserted 2705 into an occluded vessel of a patient. The apparatus includes a catheter with an extended body and an intravascular imaging device disposed on a distal portion thereof. At a distal end of extended body is an exit port. The imaging device is used for imaging 2709 the vessel to obtain a 3D image. A crossing member disposed within a lumen in the catheter is extended 2717 from the catheter, away from the distal end of the extended body, and used to cross 2719 through the CTO. Any suitable apparatus may be used that includes a member for crossing a CTO and an intravascular imaging device. For example, any device shown herein or any device with any combination of features shown herein may be used in the method 2701 for crossing a CTO according to the invention.

Additional features that may optionally be included on or with an apparatus of the invention relate to functional measurement. Functional measurement generally relates to measuring a quality or property of fluid within a vessel such as pressure, velocity, temperature or to making indirect measurements such as of coronary flow reserve or fractional flow reserve.

In some embodiments, a pressure sensor (or a flow velocity sensor, or a combination sensor) is additionally or alternatively placed on a catheter of the device or a guidewire for use in methods, devices, and kits of the invention.

Figure 28:
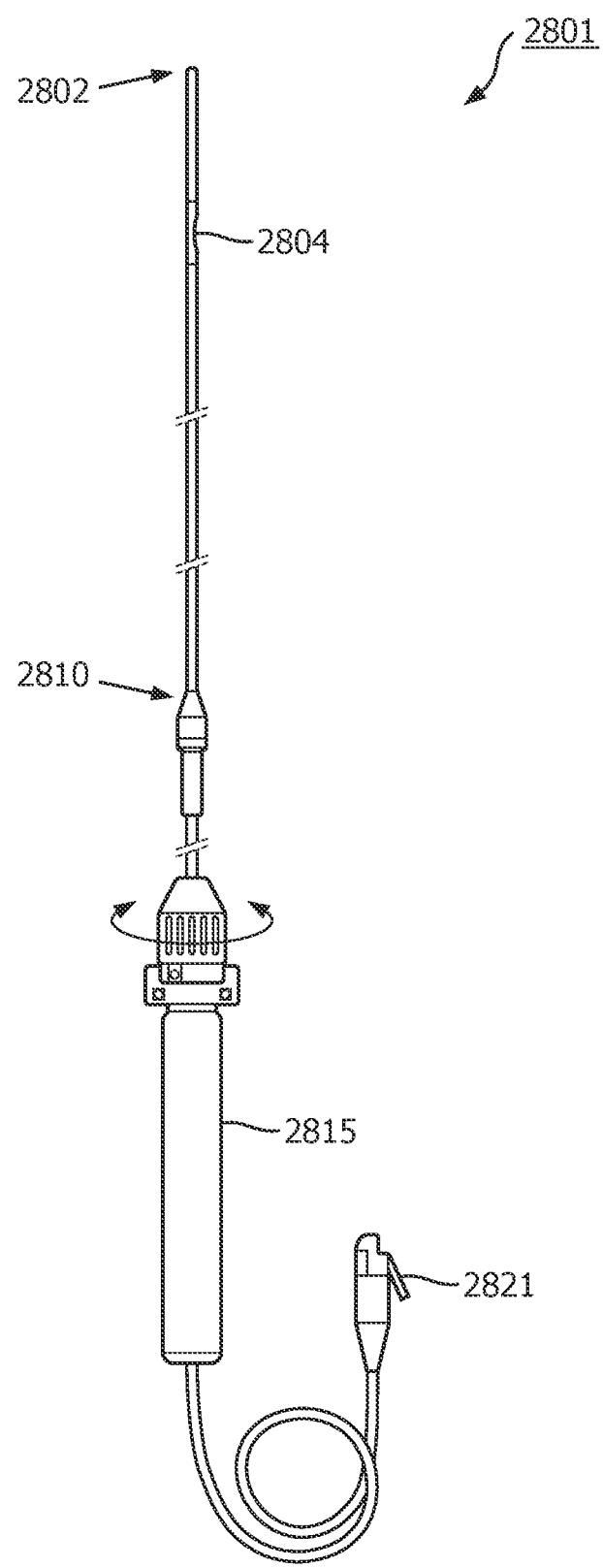
FIG. 28 illustrates a guidewire with a pressure sensor.

FIG. 28 illustrates a guidewire 2801 with a pressure sensor 2804. Guidewire 2801 generally defines an elongated body extending from a proximal end 2810 to a distal end 2802. Proximal end 2810 connects to connector housing 2815, which offers a modular plug 221 for connection to a computing device in systems of the invention.

A pressure sensor allows one to obtain pressure measurements within a body lumen. A particular benefit of pressure sensors is that pressure sensors allow one to measure of fractional flow reserve (FFR) in vessel, which is a comparison of the pressure within a vessel at positions on either side of the shunt. The level of FFR determines the patency of, for example, a newly-crossed CTO.

Pressure sensor 2804 can be mounted on the distal portion of a flexible elongate member including, for example, on one of the device shown in FIG. 1 or FIG. 3. In certain embodiments, the pressure sensor is positioned distal to a compressible and bendable coil segment of the elongate member as shown in FIG. 28. This allows the pressure sensor to move away from the longitudinal axis and coil segment as bended. The pressure sensor can be formed of a crystal semiconductor material having a recess therein and forming a diaphragm bordered by a rim. A reinforcing member is bonded to the crystal and reinforces the rim of the crystal and has a cavity therein underlying the diaphragm and exposed to the diaphragm. A resistor having opposite ends is carried by the crystal and has a portion thereof overlying a portion of the diaphragm. Electrical conductor wires can be connected to opposite ends of the resistor and extend within the flexible elongate member to the proximal portion of the flexible elongate member. Additional details of suitable pressure sensors that may be used with devices of the invention are described in U.S. Pat. No. 6,106,476, which describes suitable methods for mounting the pressure sensor 3004 within a sensor housing. As discussed above, additionally or alternatively, an apparatus of the invention or a guidewire for use therewith can include a flow sensor. In some embodiments, a guidewire is used that includes a flow sensor. A suitable product for guidewire 2801 is the PrimeWire PRESTIGE from Volcano Corporation. Preferably the guidewire includes of a flexible elongate element having proximal and distal ends and a diameter of 0.018" or less as disclosed in U.S. Pat. Nos. 5,125,137, 5,163,445, 5,174,295, 5,178,159, 5,226,421, 5,240,437 and 6,106,476, each incorporated by reference.

A guidewire of the invention may include a flexible elongate element having proximal and distal extremities, and can be formed of a suitable material such as stainless steel, Nitinol, polyimide, PEEK or other metallic or polymeric materials having an outside diameter for example of 0.018" or less and having a suitable wall thickness, such as, e.g., 0.001" to 0.002". This flexible elongate element is conventionally called a hypotube. In one embodiment, the hypotube may have a length of less than 280 cm, preferably about 50, 310, 70, or 80 cm. Typically, such a guide wire may further include a stainless steel core wire extending from the proximal extremity to the distal extremity of the flexible elongate element to provide the desired torsional properties to facilitate steering of the guide wire in the vessel and to provide strength to the guidewire and prevent kinking. The guidewire can have a diameter of about 0.014" (0.35 mm) and can include the functional instrumentation of the Doppler guide wire sold under the name FLOWIRE by Volcano Corporation, the pressure guidewire sold under the name PRIMEWIRE PRESTIGE by Volcano Corporation, or both.

Guidewire 2801 with a pressure sensor 2804 may be used to measure pressure and thus a pressure gradient may be measured. Depending on the pressure or velocity gradient measured across a newly-crossed CTO it may be determined when the procedure is successful. Guidewire 2801 measures blood pressure on one side of the CTO site. Once the value is stabilized and recorded, pressure sensor 2804 is moved to the other side of the CTO site, and the blood pressure is again recorded. This can provide pressure values across the CTO site to aid in evaluating the procedure.

Additionally or alternatively, blood flow velocity may be measured using a guidewire with a functional measurement sensor.

Figure 29:
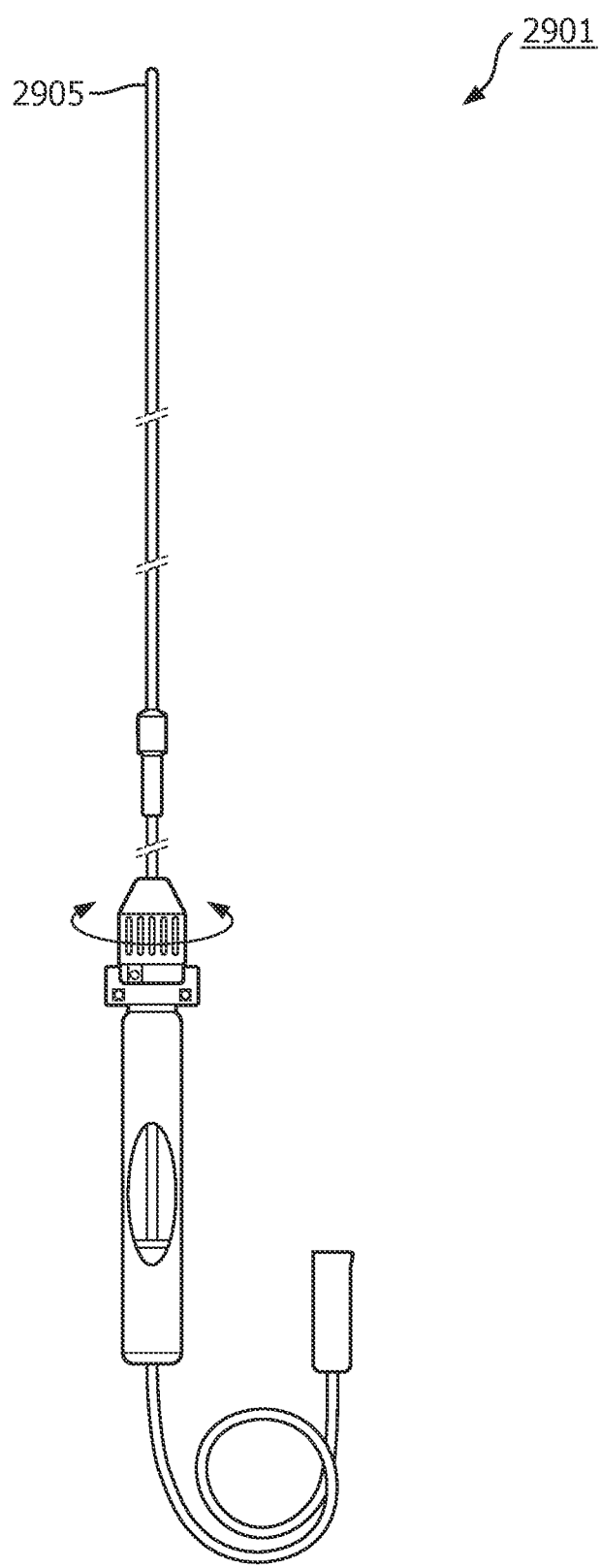
FIG. 29 illustrates a guidewire with a flow sensor.

FIG. 29 illustrates a guidewire 2901 with a flow sensor 2905. The flow sensor can be used to measure blood flow velocity within the vessel, which can be used to assess coronary flow reserve (CFR), or similar. The flow sensor can be, for example, an ultrasound transducer, a Doppler flow sensor or any other suitable flow sensor, disposed at or in close proximity to the distal tip of the guidewire. The ultrasound transducer may be any suitable transducer, and may be mounted in the distal end using any conventional method, including the manner described in U.S. Pat. Nos. 5,125,137, 6,551,250 and 5,873,835. A suitable product for guidewire 2901 with a flow sensor 2905 is the FLOWIRE from Volcano Corporation.

In a preferred embodiment, methods of the invention employ a guidewire that includes a device for measuring pressure and a device for measuring flow, i.e., a combination tip.

Figure 30:
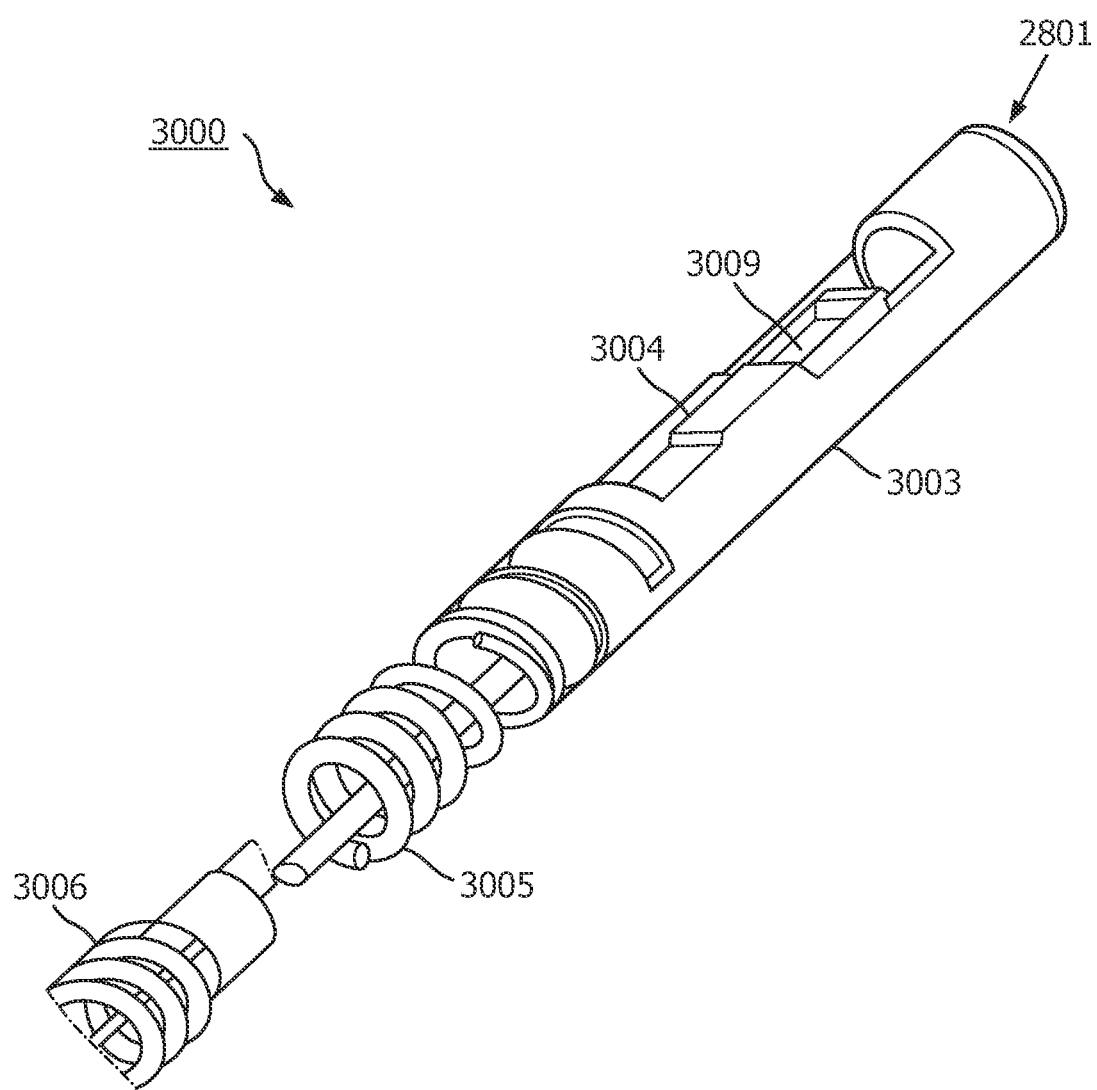
FIG. 30 shows a combination sensor tip for use with an apparatus of the invention.

FIG. 30 shows a combination sensor tip 3000 of a guidewire 2801 according to embodiments of the present invention. The combination sensor tip 3000 includes a pressure sensor 3004 within sensor housing 3003, and optionally includes a radiopaque tip coil 3005 distal to proximal coil 3006. Combination sensor tip includes an ultrasound transducer 3009 disposed therein. The ultrasound transducer 3009 may be any suitable transducer, and may be mounted in the distal end using any conventional method, including the manner described in U.S. Pat. No. 5,125,137, which is fully incorporated herein by reference. Conductors (not shown) may be secured to the front and rear sides of the ultrasound transducer 3009, and the conductors may extend interiorly to the proximal extremity of a guide wire.

The combination sensor tip 3000 also includes a pressure sensor 3004 in close proximity to the distal end 2802 of the combination sensor tip 3000. The pressure sensor 3004 may be of the type described above. The combination sensor tip 3000 is advantageous because by having both the ultrasound transducer 3009 and the pressure sensor 3004 near its distal end, the combination sensor tip 3000 is capable of being positioned distally beyond the CTO site. Additionally, the combination sensor tip 3000 is able to take measurements from the ultrasound transducer 3009 and the pressure 104 at approximately the same location and approximately the same time. Constructions suitable for use with a guidewire of the invention are discussed in U.S. Pub. 2013/0030303 to Ahmed, the contents of which are incorporated by reference.

Figure 31:
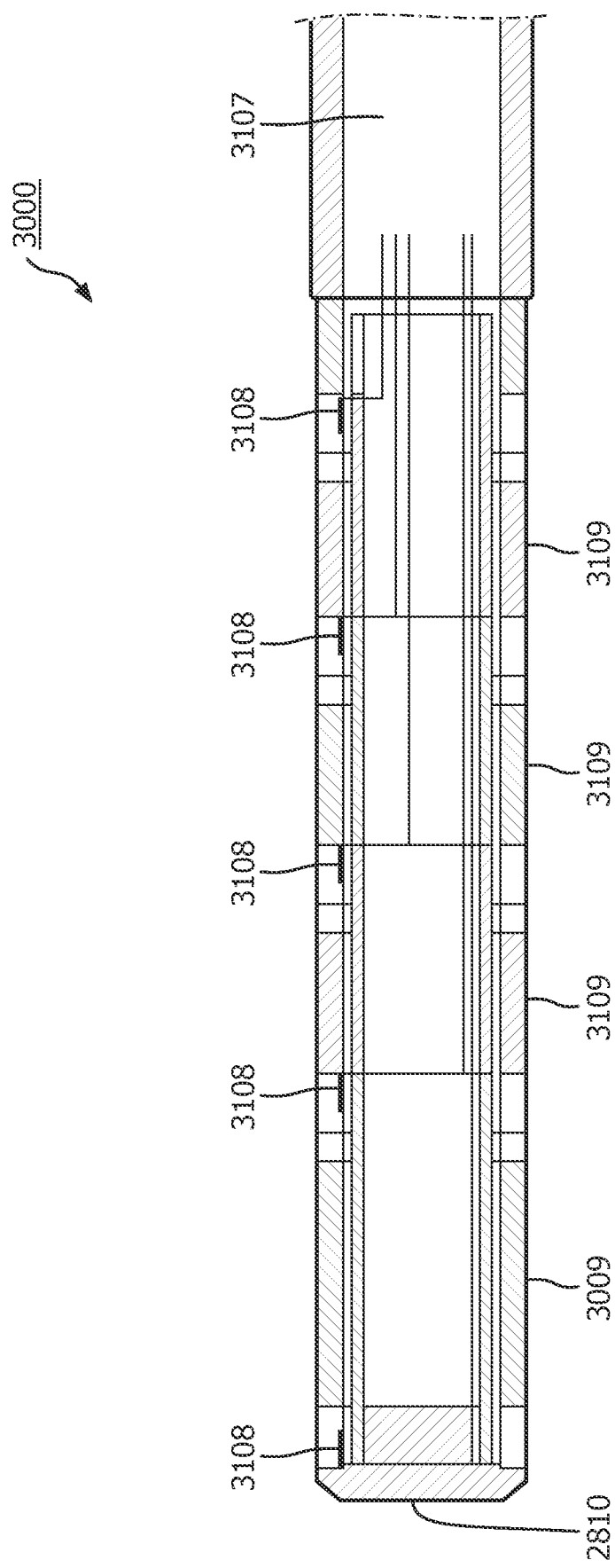
FIG. 31 shows wire conductors in a device with a combination sensor tip.

FIG. 31 shows fine wire conductors 3107 passing through the guide wire to conductive bands 3108 near the proximal end 2810 of the guide wire. Signals from the ultrasound transducer 3009 and the pressure sensor 3004 may be carried by conductors 3107. Usually three electrical connectors are necessary for a stand-alone pressure measurement guidewire and two electrical connectors are necessary for a stand-alone flow measurement guidewire. A guide wire incorporating the combination sensor tip 3000 of the present invention includes electrical conductors 3107 extending through the lumen of the guidewire and conductive bands 3108 on the proximal end of the guidewire. The conductive bands 3108 may be electrically isolated from each other by means of epoxy 3109. Alternatively, polyimide tubes may be used to isolate conductors from the conductive bands.

The electrical connection wires can include a conductive core made from a conductive material, such as copper, and an insulating coating, such as a polyimide, Fluoro-polymer, or other insulating material. The electrical connection wires extend from one or more sensors located on the distal end of the guidewire, run down the length of the guidewire, and connect to a connector housing at a proximal end.

Any suitable arrangement of the electrical connection wires through the length of the elongate member can be used. The arrangement of electrical connection wires provides for a stable connection from the proximal end to the distal end of the guidewire. Preferably, a proximal end connects to connector housing 2815 as shown in FIG. 28. In certain embodiments, the electrical connector wires are joined together to form a male connector at a proximal end. The male connector mates with a female connector of the connector housing. The termination of the male connector can be performed by a metal deposition process as described in U.S. Pat. No. 6,210,339 or by laser direct structuring as described in U.S. Pub. 2014/0179179, both incorporated herein by reference in its entirety. The deposited metal (or any conductive material) permanently adheres or couples to the exposed conductive wires at points where the polyimide layers were removed. After the masking material is removed, there are independent conductive stripes, each connected to a different respective electric wire. Because of the precision nature of the winding process as well as the masking and metal deposition processes, a male connector is made that is short in length, yet very reliable, in mating with a female connector and cable. Alternatively, conductive bands may be coupled to the exposed ends of the electric wires instead of the metallizing process.

The connector housing can be connected to an instrument, such as a computing device (e.g. a laptop, desktop, or tablet computer) or a physiology monitor, that converts the signals received by the sensors into pressure and velocity readings in systems of the invention.

As discussed above, methods and devices of the invention may include one or any combination of intravascular imaging sensor, pressure sensor, flow sensor, or combination sensor tip 3000. Data collected from such devices may be received at an imaging instrument, computer system, or both.

Figure 32:
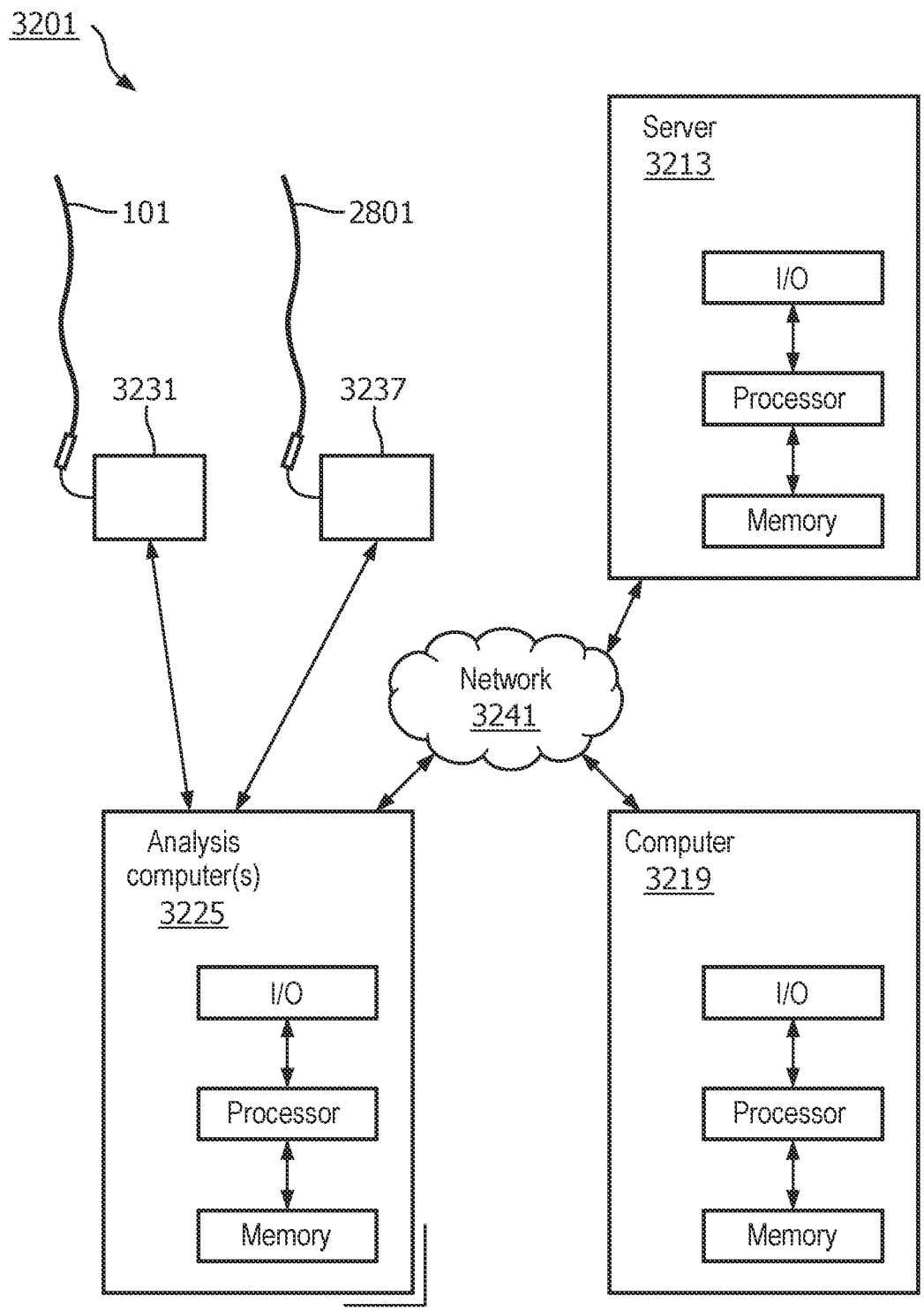
FIG. 32 illustrates a system according to certain embodiments of the invention.

FIG. 32 illustrates a system 3201 for use of a combo guidewire 2801 with an apparatus 101 of the invention. Data collected by the intravascular imaging device 175 on apparatus 101 is initial processed by imaging processor 3231 (e.g., the base station for an IVUS system). Data collected by combo guidewire 2801 may initial be processed by subsystem 3237 (e.g., by a field-programmable gate array or other processing chip) as needed for analysis. Those data are then integrated by analysis computer 3225, which includes a processor coupled to a non-transitory memory and one or more input/output (I/O) devices. Preferably, one of the I/O devices is a monitor for displaying an IVUS image captured by imaging device 175. System 3201 may also include either or both of a server computer 3213 or an additional workstation computer 2119. In general, each computer device will include a processor coupled to a non-transitory memory and one or more input/output (I/O) devices A processor can be taken to mean one or more silicon chips, the processing cores thereof, or any combination of the chips and cores, that operate together to perform computing operations. For example, the processor sold under the trademark 17 by Intel Corporation (Santa Clara, Calif.) is a processor suitable for use in system 3201.

Memory generally includes one or more devices for random access, storage, or both. Preferably, memory includes a tangible, non-transitory computer readable medium, and may be provided by one or more of a solid state drive (SSD), a magnetic disc drive (aka, "a hard drive"), flash memory, an optical drive, others, or a combination thereof.

An I/O device may include one or more of a monitor, keyboard, mouse, touchscreen, Wi-Fi card, cell antenna, Ethernet port, USB port, light, accelerometer, speaker, microphone, drive for removable disc, others, or a combination thereof. Preferably, any combination of computer in system 1601 may communicate through the use of a network, which may include communication devices for internet communication, telephonic communication, others, or a combination thereof.

Although the apparatus 101 itself is an imaging device, in some methods of using the invention, a second imaging catheter are used. FIG. 32 also illustrates a system in which an apparatus 101 is used with a second imaging catheter wherein catheter 2801 is an intravascular imaging catheter. Apparatus 101 provides puncturing catheter for use in the vessel with the CTO. But in this embodiment, the imaging catheter 2801 is used in an adjacent vessel. The imaging catheter in the adjacent vessel is close enough to image the occluded vessel and gauge how far the CTO extends. This increases safety when using the puncturing catheter.

While the above devices and methods are especially suitable for treating CTOs in the legs, they can also be used for other indications, such as resolving aneurysms, neurological procedures, and treatment of stroke.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. An apparatus for crossing a chronic total occlusion (CTO), the apparatus comprising:
an extended body having a proximal portion and a distal portion terminating in a distal end, wherein the distal end is configured for insertion into a vessel of a patient;
an intravascular imaging device on the distal portion of the extended body;
an exit port on the distal end of the extended body; and
a crossing member within a lumen in the extended body and configured to be pushed out of the exit port and thereby extended away from the distal end of the extended body, the crossing member comprising a tip configured to cross through the CTO within a true lumen of the vessel;
a spring located at the proximal portion of the extended body, wherein the spring is coupled to the crossing member, wherein the spring extends axially and exerts an axial force on the crossing member; and
a catch located at the proximal portion of the extended body adjacent to and in mechanical communication with the spring, wherein the catch comprises:
a central pivot point;
a first portion disposed on a first side of the central pivot point; and
a second portion disposed on an opposite side of the central pivot point from the first portion, the second portion configured to engage a pushable surface operably connected to the spring;
wherein upon engagement of the catch, the axial force exerted by the spring is restrained by an engagement of the second portion of the catch with the pushable surface, and wherein upon release of the catch, the axial force exerted by the spring is transmitted through the extended body by a disengagement of the second portion of the catch with the pushable surface to push the crossing member axially relative to the extended body and to cause the crossing member to extend axially out of the exit port at the distal end of the extended body and cross the CTO, wherein the catch pivots in response to actuation by the operator of the first portion of the catch to thereby release the axial force exerted by the spring.

2. The apparatus of claim 1, wherein the proximal portion of the extended body provides a handle for operation by an operator of the apparatus.

3. The apparatus of claim 2, wherein the catch extends outward from the apparatus for actuation by the operator.

4. The apparatus of claim 1, further comprising a balloon for treatment.

5. The apparatus of claim 1, further comprising a self-centering feature.

6. The apparatus of claim 5, wherein the self-centering feature comprises a balloon.

7. The apparatus of claim 5, wherein the self-centering feature comprises an expandable funnel braid or helical cage apparatus.

8. The apparatus of claim 7, wherein the expandable funnel braid comprises a shape memory alloy.

9. The apparatus of claim 1, wherein the tip defines a sharpened needle point.

10. The apparatus of claim 1, wherein the tip defines a blunt end.

11. The apparatus of claim 1, wherein the tip comprises two or more prongs configured to break through a cap of the CTO.

12. The apparatus of claim 1, wherein the tip comprises one or more burs.

13. The apparatus of claim 1, wherein the tip defines a drill mechanism.

14. The apparatus of claim 1, wherein the tip is configured to deliver radio frequency (RF) energy to disrupt the CTO.

15. The apparatus of claim 14, wherein the tip delivers the RF energy via a monopolar mechanism using at least one electrode placed outside of a body of the patient.

16. The apparatus of claim 1, further comprising a jet lumen.

17. The apparatus of claim 16, wherein the jet lumen is configured to deliver fluid to the CTO.

18. The apparatus of claim 17, wherein the jet lumen is configured to deliver a lytic agent.

19. The apparatus of claim 1, further comprising a cutting balloon.

20. The apparatus of claim 1, further comprising a deflectable tip mechanism to steer the tip towards an area of interest.

21. The apparatus of claim 20, wherein the deflectable tip comprises a shape set nitinol with a telescoping feature configured to aid deflection.

22. The apparatus of claim 1, further comprising a delivery mechanism for injecting drugs through the tip of the crossing member into a cap of the CTO.

23. The apparatus of claim 1, wherein the crossing member comprises a flexural modulus of about 20 GPa.

24. The apparatus of claim 1, wherein the catch comprises a detent mechanism.

* * * * *